United States Patent
Asano

(10) Patent No.: US 12,258,583 B2
(45) Date of Patent: Mar. 25, 2025

(54) EMBRYONIC ERYTHROBLAST-CONTAINING CELL POPULATION AND METHOD FOR PRODUCING SAME, CELL CULTURE COMPOSITION, AND COMPOUND TEST METHOD

(71) Applicant: SUMITOMO CHEMICAL COMPANY, LIMITED, Tokyo (JP)

(72) Inventor: Kouji Asano, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 909 days.

(21) Appl. No.: 17/416,044

(22) PCT Filed: Dec. 19, 2019

(86) PCT No.: PCT/JP2019/049774
§ 371 (c)(1),
(2) Date: Jun. 18, 2021

(87) PCT Pub. No.: WO2020/130068
PCT Pub. Date: Jun. 25, 2020

(65) Prior Publication Data
US 2022/0049220 A1    Feb. 17, 2022

(30) Foreign Application Priority Data

Dec. 20, 2018  (JP) ................. 2018-238784

(51) Int. Cl.
*C12N 5/078*    (2010.01)
*C12N 5/0735*   (2010.01)
*C12N 5/074*    (2010.01)

(52) U.S. Cl.
CPC ......... *C12N 5/0641* (2013.01); *C12N 5/0606* (2013.01); *C12N 5/0696* (2013.01); *C12N 2501/105* (2013.01); *C12N 2501/2303* (2013.01); *C12N 2501/2311* (2013.01); *C12N 2501/30* (2013.01); *C12N 2506/1353* (2013.01)

(58) Field of Classification Search
CPC ... C12N 5/0641; C12N 5/0634; C12N 5/0606
See application file for complete search history.

(56) References Cited

U.S. PATENT DOCUMENTS

| | | |
|---|---|---|
| 2003/0153082 A1 | 8/2003 | Bhatia |
| 2010/0222347 A1 | 9/2010 | Ashikawa et al. |
| 2011/0086424 A1 | 4/2011 | Lanza et al. |
| 2011/0151554 A1 | 6/2011 | Yuo et al. |
| 2013/0011924 A1 | 1/2013 | Niwa et al. |
| 2015/0218112 A1 | 8/2015 | Altamura et al. |
| 2016/0194607 A1 | 7/2016 | Douay et al. |

FOREIGN PATENT DOCUMENTS

| | | |
|---|---|---|
| JP | 2012-519005 A | 8/2012 |
| JP | 2013-520164 A | 6/2013 |
| JP | 2013-521762 A | 6/2013 |
| JP | 2015-522290 A | 8/2015 |
| JP | 2015-524459 A | 8/2015 |
| JP | 2016-525882 A | 9/2016 |
| JP | 2016-187354 A | 11/2016 |
| WO | WO 2008/056779 A1 | 5/2008 |
| WO | WO 2009/041072 A1 | 4/2009 |
| WO | WO 2010/099539 A1 | 9/2010 |
| WO | WO 2011/101468 A1 | 8/2011 |
| WO | WO 2014/013255 A1 | 1/2014 |
| WO | WO 2014/023754 A1 | 2/2014 |
| WO | WO 2014/186508 A1 | 11/2014 |
| WO | WO 2018/067826 A1 | 4/2018 |

OTHER PUBLICATIONS

Chang (2006, Blood, 108(5):1515-1523).*
Ng (2005, Blood, 106(5):1601-1603).*
Yanai (2013, Tissue Engineering, 19(10), p. 755-764).*
"ROCK Inhibitor Y-27632," StemCell Technologies, Aug. 8, 2016, 3 pages total.
European Communication pursuant to Article 94(3) EPC for European Application No. 19900589.3, dated Dec. 22, 2023.
Kingsley et al., ""Maturational" globin switching in primary primitive erythroid cells," Blood, vol. 104, No. 4, 2006, pp. 1665-1672.
Ley et al., "Globin Gene Expression in Erythroid Human Fetal Liver Cells," Journal of Clinical Investigation, vol. 83, No. 3, 1989, pp. 1032-1038.
Peschle et al., "Haemoglobin switching in human embryos: asynchrony of $\zeta \rightarrow \alpha$ and $\epsilon \rightarrow \gamma$-globin switches in primitive and definitive erythropoietic lineage," Nature, vol. 313, 1985, pp. 235-238.
Fujita et al., "β-Globin-Expressing Definitive Erythroid Progenitor Cells Generated from Embryonic and Induced Pluripotent Stem Cell-Derived Sacs," Stem Cells, vol. 34, No. 6, 2016, pp. 1541-1552.
International Search Report (PCT/ISA/210) issued in PCT/JP2019/049774, dated Mar. 17, 2020.
Ochi et al., "Multicolor Staining of Globin Subtypes Reveals Impaired Globin Switching During Erythropoiesis in Human Pluripotent Stem Cells," Stem Cells Translational Medicine, vol. 3, 2014, pp. 792-800.
Takayama et al., "Generation of functional platelets from human embryonic stem cells in vitro via ES-sacs, VEGF-promoted structures that concentrate hematopoietic progenitors," Blood, vol. 111, No. 11, 2008, pp. 5298-5306.

(Continued)

*Primary Examiner* — Valarie E Bertoglio
(74) *Attorney, Agent, or Firm* — Birch, Stewart, Kolasch & Birch, LLP

(57) ABSTRACT

Provided is a method for producing a cell population containing embryonic erythroblasts, including the steps of: (1) subjecting pluripotent stem cells to suspension culture to form a cell aggregate; and (2) obtaining the cell population from the cell aggregate obtained in step (1), step (2) including step (2a) of subjecting the cell aggregate to adhesion culture. In addition, provided are an embryonic erythroblast-containing cell population, a cell culture composition containing the cell population, and a compound test method that uses the embryonic erythroblast-containing cell population.

13 Claims, 11 Drawing Sheets

(56) References Cited

OTHER PUBLICATIONS

Yokoyama, "Hematopoietic stem cells and mature blood cells from pluripotent stem cells," Nippon Rinsho, vol. 69, No. 12, 2011, pp. 2137-2141.
Taiwanese Office Action for Taiwanese Application No. 108146791, dated Nov. 9, 2023, with an English translation.
Chinese Office Action and Search Report for Chinese Application No. 201980084002.4, dated Feb. 23, 2024, with English translation.
Dias et al., "Generation of Red Blood Cells from Human Induced Pluripotent Stem Cells," Stem Cells and Development, vol. 20, No. 9, 2011, pp. 1639-1647.
European Communication pursuant to Article 94(3) EPC for European Application No. 19900589.3, dated Jun. 9, 2023.
Doulatov et al., "Drug Discovery for Diamond-Blackfan Anemia Using Reprogrammed Hematopoietic Progenitors", HHS Public Access, Author Manuscript, Sci Transl Med., vol. 9, No. 376, Feb. 8, 2017 (available in PMC August 8. 2017), pp. 1-26.
Extended European Search Report for European Application No. 19900589.3, dated Aug. 3, 2022.
Mao et al., "Early Development of Definitive Erythroblasts from Human Pluripotent Stem Cells Defined by Expression of Glycophorin A/CD235a, CD34, and CD36", ScienceDirect, vol. 7, No. 5, Nov. 8, 2016, pp. 869-883 (19 pages total).
Japanese Office Action for Japanese Application No. 2020-561501, dated Oct. 3, 2023, with an English translation.

* cited by examiner

EMBRYONIC ERYTHROBLAST-CONTAINING CELL POPULATION AND METHOD FOR PRODUCING SAME, CELL CULTURE COMPOSITION, AND COMPOUND TEST METHOD

TECHNICAL FIELD

The present invention relates to an embryonic erythroblast-containing cell population and a production method thereof, and a cell culture composition containing the cell population. The invention further relates to a compound test method that uses the cell population.

BACKGROUND ART

In a developmental toxicity test for compounds, it has been known that erythrocyte function inhibitory compounds such as hemoglobin synthesis inhibitors inhibit the development of fetus and induce teratogenicity and/or embryonic lethality. Meanwhile, the globin gene, which participates in erythrocyte oxygen delivery, has been known to be involved in a switching phenomenon in which the gene expression is changed, in sequence, from an embryonic form via a fetal form to an adult form during ontogenetic development.

Thus, to evaluate teratogenicity caused by the erythrocyte function inhibition exerted by a compound in an in vitro test system, it seems to be accurate and effective to use embryonic erythroblasts, which are blood cells in a critical period of teratogenicity, for the evaluation.

Non-Patent Literature 1 (Fujita A. et al., Stem Cells, 2016 June, 34(6): 1541-52) discloses a method for producing erythroblasts expressing a high level of β-globin from human embryonic stem cells or induced pluripotent stem cells while the erythroblasts undergo expression of ε-globin.

CITATION LIST

Non Patent Literature

NPL 1: Fujita A. et al., Stem Cells, 2016 June, 34(6): 1541-52.

SUMMARY OF INVENTION

Technical Problem

However, the method disclosed in Non-Patent Literature 1 needs sophisticated skills. Thus, the method cannot be necessarily said to be sufficiently reproducible as a method for producing a cell population containing embryonic erythroblasts that express ε-globin. The purpose of the invention is to provide a method for producing, in a reproducible manner, an embryonic erythroblast-containing cell population from pluripotent stem cells, a cell population that can be obtained by the production method, and a cell culture composition containing the cell population. In addition, another purpose of the invention is to provide a compound test method that uses the embryonic erythroblast-containing cell population.

Solution to Problem

The invention provides an embryonic erythroblasts-containing cell population and a production method thereof, a cell culture composition, and a compound test method as exemplified below.

[1] A method for producing a cell population containing embryonic erythroblasts, comprising:
(1) subjecting pluripotent stem cells to suspension culture to form a cell aggregate;
(2) obtaining the cell population from the cell aggregate obtained in step (1), and wherein step (2) comprising step (2a) of subjecting the cell aggregate to adhesion culture.

[2] The production method according to [1], wherein step (2) further comprises step (2b) of collecting the cell population.

[3] The production method according to [1] or [2], wherein at least 70% of cells included in the cell population are the embryonic erythroblasts.

[4] The production method according to any one of [1] to [3], wherein at least 50% of β-globin gene family expressed in cells of the cell population is ε-globin gene.

[5] The production method according to any one of [1] to [4], wherein step (1) is carried out using non-cell-adherent cultureware.

[6] The production method according to any one of [1] to [5], wherein step (2a) is carried out using cell-adherent cultureware.

[7] The production method according to [6], wherein the cell-adherent cultureware is coated with a basement membrane preparation.

[8] The production method according to any one of [1] to [7], wherein step (1) follows a step of dispersing the pluripotent stem cells. [9] The production method according to any one of [1] to [8], wherein step (1) comprises a step of centrifuging the pluripotent stem cells.

[10] The production method according to any one of [1] to [9], wherein a time from start of step (1) to start of step (2a) is 12 h or more and 96 h or less.

[11] The production method according to any one of [1] to [10], wherein a culture period of step (2a) is 2 days or more and 18 days or less.

[12] The production method according to any one of [1] to [11], wherein at least one step selected from the group consisting of step (1) and step (2a) is performed in the presence of a ROCK inhibitor.

[13] The production method according to any one of [1] to [12], wherein step (2a) is performed in the presence of at least one selected from the group consisting of erythropoietin, erythropoietin receptor-activating substance, and erythropoietin receptor-mediated signaling pathway-activating substances.

[14] The production method according to any one of [1] to [13], wherein step (2a) is carried out in the presence of feeder cells. [15] The production method according to [14], wherein the feeder cells are bone marrow stromal cells or a bone marrow stromal cell-derived cell line.

[16] The production method according to [15], wherein the feeder cells are OP9 cells.

[17] The production method according to any one of [1] to [16], wherein step (2a) is performed in the presence of at least one selected from the group consisting of stem cell factor, interleukin 3, interleukin 11, hydrocortisone, and insulin-like growth factor.

[18] The production method according to any one of [1] to [17], wherein the pluripotent stem cells are primate pluripotent stem cells or rodent pluripotent stem cells.

[19] The production method according to any one of [1] to [17], wherein the pluripotent stem cells are human pluripotent stem cells or rat pluripotent stem cells.

[20] A compound test method using a cell population containing embryonic erythroblasts, comprising:
(A) subjecting pluripotent stem cells to suspension culture to form a cell aggregate;
(B) obtaining the cell population from the cell aggregate obtained in step (A);
(C) culturing the cell population in the presence of a test compound; and
(D) measuring at least one metric selected from the group consisting of 1) a cell count, 2) cell viability, 3) a heme concentration, 4) a protoporphyrin IX concentration, and 5) a globin expression level of the cell population cultured in step (C),
wherein step (B) comprises step (Ba) of subjecting the cell aggregate to adhesion culture.

[21] The compound test method according to [20], wherein step (B) further comprises step (Bb) of collecting the cell population.

[22] The compound test method according to [20] or [21], wherein at least 70% of cells included in the cell population are the embryonic erythroblasts.

[23] The compound test method according to any one of [20] to [22], wherein at least 50% of β-globin gene family expressed in cells of the cell population is ε-globin gene.

[24] The compound test method according to any one of [20] to [23], wherein step (C) is carried out in an absence of feeder cells.

[25] The compound test method according to any one of [20] to [24], wherein step (C) is performed in an absence of at least one selected from the group consisting of interleukin 3, interleukin 11, hydrocortisone, and insulin-like growth factor.

[26] The compound test method according to any one of [20] to [25], wherein a culture period of step (C) is 2 days or more.

[27] The compound test method according to any one of [20] to [26], wherein the pluripotent stem cells are primate pluripotent stem cells or rodent pluripotent stem cells.

[28] The compound test method according to any one of [20] to [26], wherein the pluripotent stem cells are human pluripotent stem cells or rat pluripotent stem cells.

[29] The compound test method according to any one of [20] to [28], wherein the compound test method uses a cell population containing embryonic erythroblasts derived from each of a plurality of biological species; and
in step (D), the measurement is carried out on the cell population obtained from pluripotent stem cells derived from each of the plurality of biological species.

[30] The compound test method according to [29], wherein the plurality of biological species comprise at least two biological species belonging to the group consisting of primates and rodents.

[31] The compound test method according to [29], wherein the plurality of biological species comprise a human and a rat.

[32] A cell population comprising embryonic erythroblasts, wherein at least 70% of cells included in the cell population are the embryonic erythroblasts.

[33] A cell population comprising embryonic erythroblasts, wherein at least 50% of β-globin gene family expressed in cells thereof is ε-globin gene.

[34] The cell population according to [32] or [33] or a cell population obtained by the production method according to any one of [1] to [19], which is used in a compound test method.

[35] The cell population according to [32] to [34] or a cell population obtained by the production method according to any one of [1] to [19], which is stored while expression of ε-globin is maintained.

[36] A cell culture composition comprising: the cell population according to any one of [32] to [35] or a cell population obtained by the production method according to any one of [1] to [19]; and a medium.

[37] The cell culture composition according to [36], wherein the medium is free of at least one selected from the group consisting of interleukin 3, interleukin 11, hydrocortisone, and insulin-like growth factor.

Advantageous Effects of Invention

The invention makes it possible to provide a method for producing, in a reproducible manner, a cell population containing embryonic erythroblasts from pluripotent stem cells and a cell population that can be obtained by the production method as well as a cell culture composition containing the cell population. In addition, the invention also makes it possible to provide a compound test method that uses the cell population containing embryonic erythroblasts.

BRIEF DESCRIPTION OF DRAWINGS

FIG. 12 shows the results of measuring (A) a heme concentration, (B) a protoporphyrin IX concentration, (c) a viable cell count, and (D) viability.

DESCRIPTION OF EMBODIMENTS

1. Definitions

Figure 1:
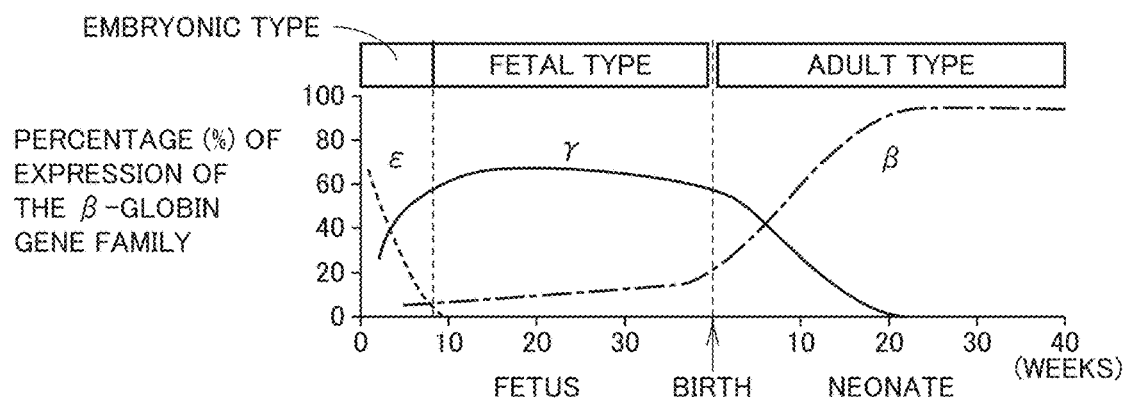
FIG. 1 is a graph showing switching of expression of the β-globin gene family in erythroblasts during human development.

As used herein, definitions of the following terms are as described below. The "stem cell(s)" means an undifferentiated cell(s) having differentiation potential and proliferation capacity (in particular, self-renewing capacity) with the differentiation potential. Examples of the stem cell(s) include, depending on their differentiation capability, subpopulations such as a pluripotent stem cell(s), a multipotent stem cell(s), or a unipotent stem cell(s). The "pluripotent stem cells" refer to stem cells that can be cultured in vitro and can be differentiated into all cells constituting a living organism (i.e., tissues derived from three germ layers (ectoderm, mesoderm, and endoderm)) (having pluripotency). The "multipotent stem cells" mean stem cells that can be differentiated into multiple tissues and/or cells, but not into all the types. The "unipotent stem cells" mean stem cells that can be differentiated into certain tissues and/or cells.

The pluripotent stem cells can be induced from, for instance, fertilized eggs, clone embryos, germinal stem cells, tissue stem cells, or somatic cells. Examples of the pluripotent stem cells include embryonic stem cells (ES cells), embryonic germ cells (EG cells), or induced pluripotent stem cells (iPS cells). Multi-lineage differentiating stress enduring cells (Muse cells) obtained from mesenchymal stem cells (MSC) and GS cells produced from germ cells (e.g., testes) are also included in the pluripotent stem cells.

Embryonic stem cells were first established in 1981, and have been applied to produce knock-out mice since 1989. Human embryonic stem cells were established in 1998, and have been gradually utilized in regenerative medicine. ES cells can be produced by culturing an inner cell mass on feeder cells or in a medium containing leukemia inhibitory factor (LIF). The methods for producing ES cells are disclosed in, for instance, WO 96/22362, WO 02/101057, U.S. Pat. Nos. 5,843,780, 6,200,806, and 6,280,718. Embryonic stem cells are available from given institutes, or commercially available products may be purchased. For instance, human embryonic stem cells KhES-1, KhES-2, and KhES-3 are available from Institute for Frontier Life and Medical Sciences, Kyoto University. Mouse embryonic stem cells EB5 cells and D3 strain are available from RIKEN, Japan, and American Type Culture Collection (ATCC), respectively. Nuclear transfer ES cells (ntES cells), one of ES cells, can be established from a cloned embryo created by transferring a somatic cell nucleus into an egg, from which a cell nucleus has been removed.

EG cells can be produced by culturing primordial germ cells in a medium containing mouse stem cell factor (mSCF), LIF, and basic fibroblast growth factor (bFGF) (Cell, 70: 841-847, 1992).

Induced pluripotent stem cells refer to cells obtained by reprogramming a somatic cell by, for instance, a known method to induce pluripotency. Specific examples include cells obtained by reprogramming a differentiated somatic cell such as a fibroblast, a peripheral monocyte or the like by expressing a certain combination of multiple genes selected from the reprogramming gene group including, for instance, Oct3/4, Sox2, Klf4, Myc (c-Myc, N-Myc, L-Myc), Glis1, Nanog, Sall4, lin28, and/or Esrrb to induce multiple differentiation potential. In 2006, Yamanaka and colleagues established an induced pluripotent stem cell from a mouse cell (Cell, 2006, 126(4), pp. 663-676). An induced pluripotent stem cell was also established using a human fibroblast in 2007, and has pluripotency and self-renewing capability like in embryonic stem cells (Cell, 2007, 131(5), pp. 861-872; Science, 2007, 318(5858), pp. 1917-1920; Nat. Biotechnol., 2008, 26(1), pp. 101-106). The induced pluripotent stem cells may be produced by a gene expression-mediated direct reprogramming method. In addition, induced pluripotent stem cells may be induced from a somatic cell by adding a compound(s) (Science, 2013, 341, pp. 651-654).

Examples of the somatic cell used when induced pluripotent stem cells are produced include, but are not particularly limited to, tissue-derived fibroblasts, hematopoietic cells (e.g., peripheral monocytes, T cells), hepatocytes, pancreatic cells, intestinal epithelial cells, or smooth muscle cells.

In the case of reprogramming through expression of several genes (e.g., four factors such as Oct3/4, Sox2, Klf4, and Myc) when induced pluripotent stem cells are produced, a means for expressing the genes are not particularly limited. Examples of the means for expressing the genes include infection protocols using viral vectors (e.g., retroviral vectors, lentiviral vectors, Sendai virus vectors, adenoviral vectors, adeno-associated virus vectors), gene transfer methods (e.g., a calcium phosphate method, lipofection, the RetroNectin method, electroporation) using plasmid vectors (e.g., plasmid vectors, episomal vectors), gene transfer methods (e.g., a calcium phosphate method, lipofection, electroporation) using RNA vectors, or direct protein injection.

Examples of the pluripotent stem cells also include gene-modified pluripotent stem cells. The gene-modified pluripotent stem cells may be produced using, for instance, homologous recombination technology. Examples of the gene modified on the chromosome include cell marker genes, histocompatibility antigen genes, or nerve cell dysfunction-based disease-related genes. The target gene on the chromosome may be modified by the procedure described in, for instance, Manipulating the Mouse Embryo, A Laboratory Manual, Second Edition, Cold Spring Harbor Laboratory Press (1994); Gene Targeting, A Practical Approach, IRL Press at Oxford University Press (1993); or Bio-Manual Series 8, Gene Targeting, Production of Transgenic Mice Using ES Cells, YODOSHA CO., LTD. (1995).

Specifically, a genomic gene corresponding to the target gene to be modified (e.g., a cell marker gene, a histocompatibility antigen gene, a disease-related gene), for instance, is isolated; and the isolated genomic gene is used to construct a targeting vector for homologous recombination of the target gene. The constructed targeting vector may be introduced into a stem cell, and a cell in which homologous recombination between the target gene and the targeting vector has occurred may be selected to produce a stem cell having the gene modified on the chromosome.

As a procedure for isolating a genomic gene corresponding to the target gene, it is possible to use the known protocol described in, for instance, Molecular Cloning, A Laboratory Manual, Second Edition, Cold Spring Harbor Laboratory Press (1989) or Current Protocols in Molecular Biology, John Wiley&Sons (1987-1997). A genomic DNA library screening system (manufactured by Genome Systems) or Universal GenomeWalker Kits (manufactured by Clontech) may be used to isolate a genomic gene corresponding to the target gene.

The targeting vector for homologous recombination of the target gene may be produced and the homologous recombinant clones may be efficiently selected in accordance with the protocols described in, for instance, Gene Targeting, A Practical Approach, IRL Press at Oxford University Press (1993) or Bio-Manual Series 8, Gene Targeting, Production of Transgenic Mice Using ES Cells, YODOSHA CO., LTD. (1995). As the targeting vector, it is possible to use any of replacement type or insertion type. As the selecting procedure, it is possible to use a procedure such as a positive selection, a promoter selection, a negative selection, or a poly-A selection. Examples of a procedure for selecting a homologous recombinant clone of interest from selected cell lines include Southern hybridization of genomic DNA or PCR protocols.

Examples of the "mammals" include rodents, ungulates, Carnivora, Lagomorpha, or primates. Examples of the rodents include a mouse, a rat, a hamster, or a guinea pig. Examples of the ungulates include a pig, a cow, a goat, a horse, or sheep. Examples of the Carnivora include a dog or a cat. Examples of the Lagomorpha include a rabbit. The "primates" refer to mammals belonging to the order Primates, and examples of the primates include the suborder Prosimii (e.g., lemurs, lorises, tree shrews) or the suborder Anthropoidea (e.g., monkeys, apes, humans).

The "cell adhesion" involves cell-to-cell adhesion (cell-cell adhesion) or cell-to-extracellular matrix (substratum) adhesion (cell-substratum adhesion). The cell adhesion also includes adhesion to, for instance, cell cultureware, which adhesion occurs under an in vitro artificial culture environment. A junction formed at the cell-cell adhesion is a cell-cell junction. A junction formed at the cell-substratum adhesion is a cell-substratum junction. Examples of the kind of cell adhesion include an anchoring junction, a communicating junction, or an occluding junction.

Examples of the cell-cell junction include a "tight junction" or an "adherence junction". The tight junction refers to a relatively strong cell-cell junction and may occur between specific cells such as epithelial cells. The presence of intercellular tight junction may be detected by a technique such as immunohistochemistry using, for instance, an antibody against a component of the tight junction (e.g., an anti-claudin antibody, an anti-ZO-1 antibody). The frequency of occurrence of adherence junction in cell aggregates is relatively high.

The "suspension culture" refers to culturing while cells are kept floating in a culture medium. Specifically, the suspension culture may be performed under conditions in which cells are attached neither to cultureware nor on feeder cells on cultureware (hereinafter, referred to as "cultureware, etc."). This suspension culture is distinguishable from culture performed under conditions in which cells adhere to cultureware, etc (adhesion culture). More specifically, the suspension culture refers to culturing under conditions in which a strong cell-substratum junction does not occur between cells and cultureware, etc. Those skilled in the art can easily determine whether cells being cultured are in a suspension culture state or during adhesion culture by, for instance, moving the cultureware at the time of microscopy.

The "adhesion culture" refers to culturing while cells are kept adhered to cultureware, etc. Here, the wording "cells are adhered to cultureware, etc." refers to the formation of strong cell-substratum junction, a kind of cell adhesion, between cells and cultureware, etc.

Cell aggregates during suspension culture have cell-to-cell plane attachment. Cell aggregates during suspension culture have no strong cell-substratum junction between cells and cultureware. Almost no cell-substratum junction is formed or its contribution is small even if the junction is formed. Cell aggregates during suspension culture may include the presence of endogenous cell-substratum junction.

The wording "cell-to-cell plane attachment" refers to plane attachment between cells. More specifically, the "cell-to-cell plane attachment" means that the percentage of surface area of a certain cell with respect to the area attached to a surface of another cell is, for instance, 1% or higher, preferably 3% or higher, and more preferably 5% or higher. The surface of cell may be detected by a technique such as staining with a membrane-staining reagent (e.g., DiI) or immunohistochemistry of a cell adhesion factor (e.g., E-cadherin, N-cadherin).

The cultureware used when suspension culture is performed is not particularly limited as long as the suspension culture is permitted, and can be determined, if appropriate, by those skilled in the art. Examples of such cultureware (culture apparatus) include flasks, tissue culture flasks, dishes, petridishes, tissue culture dishes, multi-dishes, microplates, microwell plates, micropores, multi-plates, multi-well plates, chamber slides, Petri dishes, tubes, trays, culture bags, spinner flasks, roller bottles, or bio-functional chips such as an organ-on-a-chip. The above cultureware is preferably non-adherent to cells so as to allow for suspension culture. It is possible to use, as non-cell-adherent cultureware, cultureware or the like, the surface of which is not treated artificially as described below for the purpose of improving adhesion to cells. In addition, it is also possible to use, as non-cell-adherent cultureware, cultureware, the surface of which is treated artificially (e.g., low protein adsorption treatment, super hydrophilic treatment with, for instance, 2-methacryloyloxyethyl phosphorylcholine (MPC) polymer) in order to decrease adhesion to cells. The bottom culturing surface of cultureware may be flat, U-shaped, or V-shaped, or may have roughness.

The cultureware used when adhesion culture is performed is not particularly limited as long as the adhesion culture is permitted, and can be determined, if appropriate, by those skilled in the art. Examples of such cultureware include flasks, tissue culture flasks, dishes, tissue culture dishes, multi-dishes, microplates, microwell plates, micropores, multi-plates, multi-well plates, chamber slides, Petri dishes, tubes, trays, culture bags, or bio-functional chips such as an organ-on-a-chip. It is possible to use, as cell-adherent cultureware, cultureware or the like, the surface of which is treated artificially for the purpose of improving adhesion to cells. Examples of the artificial treatment include coating treatment with extracellular matrix, a polymer, or the like, or surface processing such as gas plasma treatment or positive charge treatment. Examples of the extracellular matrix to which cells adhere include a basement membrane preparation, laminin, entactin, collagen, or gelatin. Examples of the polymer include polylysine or polyornithine. The bottom culturing surface of cultureware may be flat, or may have roughness.

A medium used for culturing cells in the invention may be prepared by using, as a basal medium, the medium that is usually used for culturing animal cells. Examples of the basal medium include Basal Medium Eagle (BME), BGJb medium, CMRL 1066 medium, Glasgow Minimum Essential Medium (Glasgow MEM), Improved MEM Zinc Option, Iscove's Modified Dulbecco's Medium (IMDM), Medium 199, Eagle Minimum Essential Medium (Eagle MEM), Alpha Modified Eagle Minimum Essential Medium (αMEM), Dulbecco's Modified Eagle Medium (DMEM), F-12 medium, DMEM/F12, IMDM/F12, Ham's medium, RPMI 1640, Fischer's medium, or a mixed medium thereof.

For culturing pluripotent stem cells, it is possible to use, for instance, a pluripotent stem cell culture medium using the above basal medium as a base, preferably a known embryonic stem cell or induced pluripotent stem cell medium, or a medium for culturing pluripotent stem cells under feeder-free conditions (feeder-free medium). Examples of the feeder-free medium include Essential 8 medium, TeSR medium, mTeSR medium, mTeSR-E8 medium, or StemFit medium.

The term "serum-free medium" means a medium free of non-conditioned or unpurified serum. A medium prepared by mixing purified blood-derived components or animal tissue-derived components (e.g., growth factors) is also included in the serum-free medium as long as non-conditioned or unpurified serum is not contained.

The serum-free medium may contain serum substitutes. The serum substitutes include those containing, if appropriate, for instance, albumin, transferrin, fatty acids, collagen precursors, trace elements, 2-mercaptoethanol or 3'-thiol glycerol, or equivalents thereof. Such serum substitutes may be prepared by the procedure disclosed in, for instance, WO 98/30679. Commercially available products may be utilized as the serum substitutes. Examples of the commercially available serum substitutes include Knockout Serum Replacement (manufactured by Thermo Fisher Scientific, Inc.) (hereinafter, sometimes referred to as "KSR"), Chemically-defined Lipid concentrated (manufactured by Thermo Fisher Scientific, Inc.), Glutamax (manufactured by Thermo Fisher Scientific, Inc.), B27 Supplement (manufactured by Thermo Fisher Scientific, Inc.), or N2 Supplement (manufactured by Thermo Fisher Scientific, Inc.).

The serum-free medium used for suspension culture or adhesion culture optionally contains, if appropriate, fatty acids or lipids, amino acids (e.g., non-essential amino acids), vitamins, growth factors, cytokines, antioxidants, 2-mercaptoethanol, pyruvic acid, buffers, inorganic salts, and/or the like.

To avoid complicated preparation, it is possible to use, as such serum-free medium, for instance, a mixed medium (manufactured by STEMCELL Technologies, Inc.) of STEMdiff Hematopoietic Basal Medium (sometimes referred to as "Stemdiff. basal medium") and STEMdiff Hematopoietic Supplement A (sometimes referred to as "Supp. A") or STEMdiff Hematopoietic Supplement B (sometimes referred to as "Supp. B"), Stemline II hematopoietic stem cell growth medium (manufactured by Sigma Aldrich Inc.), Hematopoietic Progenitor Medium (manufactured by Promo Cell, Inc.), STEMα. A (manufactured by STEM ALPHA, Inc.), or PRIME-XV Hematopoietic Cell Basal XSFM (manufactured by Irvine Scientific, Inc.). The serum-free medium used in the invention is preferably a mixed medium of STEMdiff Hematopoietic Basal Medium and STEMdiff Hematopoietic Supplement A or STEMdiff Hematopoietic Supplement B.

The term "serum-containing medium" means a medium containing non-conditioned or unpurified serum. This medium optionally contains fatty acids or lipids, amino acids (e.g., non-essential amino acids), vitamins, growth factors, cytokines, antioxidants, 2-mercaptoethanol, 1-monothioglycerol, pyruvic acid, buffers, inorganic salts, and/or the like.

From the viewpoint of avoiding contamination of chemically undefined components, the medium used in the invention is a medium in which components contained have been chemically defined (chemically defined medium; CDM).

The "basement membrane preparation" refers to a preparation containing basement membrane components having functions to control, for instance, epithelial cell-like cell morphology, differentiation, proliferation, movement, and/or functional expression when desired cells with basement membrane formation capability are seeded and cultured thereon. In the invention, cell aggregates when subjected to adhesion culture may be cultured in the presence of a basement membrane preparation. Here, the "basement membrane components" refer to thin film-shaped extracellular matrix molecules present between an epithelial cell layer and a stromal cell layer in an animal tissue. Examples of the basement membrane components include type IV collagen, laminin, heparan sulfate proteoglycan (perlecan), entactin/nidogen, cytokines, and/or growth factors. The basement membrane preparation may be prepared by, for instance, removing, by using a cellular lipid-dissolving solution or an alkali solution, cells that are attached via a basement membrane to the support and have basement membrane formation capability from a support. Examples of the basement membrane preparation include commercially available basement membrane preparation products (e.g., Matrigel (manufactured by Corning, Inc.)), Geltrex (manufactured by Life Technologies, Inc.), or those containing, as basement membrane components, known extracellular matrix molecules (e.g., laminin, type IV collagen, heparan sulfate proteoglycan, entactin).

The basement membrane preparation such as Matrigel (manufactured by Corning, Inc.) prepared by extraction and solubilization from tissues and cells of Engelbreth-Holm-Swarm (EHS) mouse sarcoma may be used for culturing cells and tissues in the invention. Likewise, it is also possible to use, as basement membrane components used for cell culture, human solubilized amniotic membrane (manufactured by Bioresource Application Institute Co., Ltd.), human recombinant laminin (manufactured by BioLamina, Inc.) produced in HEK293 cells, human recombinant laminin fragment (manufactured by Nippi, Inc.), human recombinant vitronectin (manufactured by Thermo Fisher Scientific, Inc.), and/or the like.

The wording "substance X-containing medium" and "in the presence of substance X" mean a medium to which an exogenous substance X is added or a medium containing an exogenous substance X, and being in the presence of exogenous substance X, respectively. The exogenous substance X is distinguishable from an endogenous substance X endogenously expressed in, secreted from, or produced from cells or tissues present in, for instance, the medium.

The "feeder cells" refer to cells other than stem cells co-existing when the stem cells are cultured. Examples of the feeder cells used for culturing pluripotent stem cells while kept undifferentiated include mouse fibroblasts (MEF), human fibroblasts, or SNL cells. Examples of the feeder cells used for inducing differentiation of pluripotent stem cells include OP9 cells, PA6 cells, or C3H10T1/2 cells (clone 8). The feeder cells are preferably feeder cells that have been subjected to growth inhibitory treatment. Examples of the growth inhibitory treatment include treatment with a growth inhibitor (e.g., mitomycin C) or γ irradiation. The feeder cells used for culturing pluripotent stem cells while kept undifferentiated can contribute to maintenance of undifferentiated pluripotent stem cells because of, for instance, secretion of liquid factors (preferably, factors for maintaining an undifferentiated state) or construction of a scaffold (extracellular matrix) for cell adhesion. The feeder cells used for inducing differentiation of pluripotent stem cells can contribute to differentiation of pluripotent stem cells into specific cells and tissues because of, for instance, secretion of liquid factors (preferably, factors for inducing differentiation) or construction of a scaffold (extracellular matrix) for cell adhesion.

The "cell aggregates" are each a mass that has been formed by assembling cells dispersed in a medium and in which cells adhere to one another. Examples of the cell aggregate include a cell mass, an embryoid body, a sphere, a spheroid, or an organoid. In the cell aggregate, cells are preferably subject to plane attachment. In some embodiments, cells may be subject to cell-to-cell adhesion in part or all of the cell aggregate or may form, for instance, an adherence junction.

The term "uniform cell aggregates" means that each cell aggregate has a certain size when the multiple cell aggregates are cultured. In the case of evaluating the size of the cell aggregates by the maximum diameter, the uniform cell aggregates mean that the deviation of the maximum diameters is small. More specifically, the term means that 75% or more of the multiple cell aggregates have the maximum diameter that is within ±100% of the average maximum diameter of the multiple aggregates, preferably within ±50% of the average maximum diameter, and more preferably within ±20% of the average maximum diameter.

The "cell population" refers to a cell group that includes 2 or more cells, and optionally includes, for instance, 1000 or more cells or $1 \times 10^4$ or more cells. The cell population may include one type of cells or may include multiple types of cells. Cells included in the cell population may be suspended in a medium or may be attached to, for instance, cultureware. In addition, cells included in the cell population may be single cells. At least part of the cells in the cell population may be subject to cell-to-cell attachment. Here, the "single cells" refer to cells with almost no cell-to-cell attachment (e.g., plane attachment). Further, the "single cells" refer to cells with almost no cell-cell junction (e.g., adherence junction) in some embodiments.

The term "dispersed" refers to separation and preferably separation into single cells by dispersing treatment such as physical treatment or enzymatic treatment of cells and tissues with cells adhered.

The "erythroblasts" represent nucleated, immature erythrocyte precursor cells in the process of development into erythrocytes. The "embryonic erythroblasts" and "embryonic erythrocytes" represent erythroblasts and erythrocytes, respectively, mainly containing ε-globin that is produced in the yolk sac as the early embryonic, primary hematopoiesis and is among the β-globin gene family. The "fetal erythroblasts" and "fetal erythrocytes" represent erythroblasts and erythrocytes, respectively, mainly containing γ-globin that is produced in the aorta-gonad-mesonephros (AGM) region and the liver and the spleen as the embryonic, secondary hematopoiesis and is among the β-globin gene family. The "adult erythroblasts" and "adult erythrocytes" represent erythroblasts and erythrocytes, respectively, mainly containing β-globin that is produced in the bone marrow after late pregnancy and is among the β-globin gene family. As used herein, the β-globin gene family refers to ε-, γ-, and β-globin genes.

The "hemoglobin" represents a protein that is contained in erythroblasts and erythrocytes in vivo and participates in oxygen delivery. Hemoglobin consists of globin proteins and hemes, which are each an iron atom-containing complex. The globin proteins in hemoglobin are a heterotetramer consisting of two globin molecules of either α- or ζ-globin and two globin molecules of either ε-, γ-, or β-globin. The ζ-globin among α- and ζ-globin molecules is expressed only during the primary hematopoiesis, but the α-globin is expressed during both the primary and secondary hematopoiesis. The early embryonic erythroblasts and erythrocytes mainly contain hemoglobin including ε-globin as subunits; the fetal erythroblasts and erythrocytes mainly contain hemoglobin including γ-globin as subunits; and the adult erythroblasts and erythrocytes mainly contain hemoglobin including β-globin as subunits. FIG. 1 illustrates the percentage of expression of the β-globin gene family expressed in erythroblasts and erythrocytes from the embryonic period to the birth or later in humans.

With reference to Table 1, heme is biologically synthesized by 8-step reactions including the following first to eighth reactions in the cytoplasm and mitochondria in erythroblasts.

During the first reaction in mitochondria, aminolevulinic acid synthetase (ALAS2) is used to synthesize δ-aminolevulinic acid from glycine and succinyl CoA.

In the second reaction, δ-aminolevulinic acid is transported from mitochondria to the cytoplasm where the δ-aminolevulinic acid is converted into porphobilinogen by aminolevulinic acid dehydrogenase (ALAD).

During the third reaction in the cytoplasm, porphobilinogen deaminase (PBGD) is used to convert porphobilinogen into hydroxymethylbilane.

During the fourth reaction in the cytoplasm, uroporphyrinogen III synthetase (URO3 S) is used to convert hydroxymethylbilane into uroporphyrinogen III.

During the fifth reaction in the cytoplasm, uroporphyrinogen III decarboxylase (UROD) is used to convert uroporphyrinogen III into coproporphyrinogen III.

In the sixth reaction, coproporphyrinogen III is transported from the cytoplasm into mitochondria where coproporphyrinogen oxidase (CPO) is used to convert coproporphyrinogen III into protoporphyrinogen IX.

During the seventh reaction in mitochondria, protoporphyrinogen IX is oxidized by protoporphyrinogen oxidase (PPO) into protoporphyrin IX (PPIX).

During the eighth reaction in mitochondria, ferrochelatase (FECH) is used to add iron to protoporphyrin IX (PPIX) to produce heme.

The resulting hemes are transported to the cytoplasm and are bound to globin proteins to become hemoglobin.

TABLE 1

| Reaction stage | Enzyme | Abbreviation | Substrate | Site of action |
|---|---|---|---|---|
| 1 | Aminolevulinic acid synthetase | ALAS2 | Glycine + Succinyl CoA | Mitochondria |
| 2 | Aminolevulinic acid dehydrogenase | ALAD | δ-Aminolevulinic acid | Cytoplasm |
| 3 | Porphobilinogen deaminase | PBGD | Porphobilinogen | Cytoplasm |
| 4 | Uroporphyrinogen III synthetase | URO3S | Hydroxymethylbilane | Cytoplasm |
| 5 | Uroporphyrinogen III decarboxylase | UROD | Uroporphyrinogen III | Cytoplasm |
| 6 | Coproporphyrinogen oxidase | CPO | Coproporphyrinogen III | Mitochondria |
| 7 | Protoporphyrinogen oxidase | PPO | Protoporphyrinogen IX | Mitochondria |
| 8 | Ferrochelatase | FECH | Protoporphyrin IX | Mitochondria |

If the function of FECH is inhibited during the eighth reaction in the heme biosynthesis pathway, protoporphyrin IX (PPIX), a substrate, accumulates.

In addition, during the seventh reaction, the function of protoporphyrinogen oxidase (PPO) may be inhibited. In this case, protoporphyrinogen IX is leaked into the cytoplasm and is spontaneously oxidized to produce protoporphyrin IX (PPIX). Since the cytoplasm does not have any ferrochelatase (FECH), protoporphyrin IX (PPIX) accumulates in the cytoplasm.

Consequently, in the case of exposure of an inhibitor for a downstream enzyme (PPO or FECH) in the biosynthesis pathway, the heme biosynthesis is blocked to accumulate protoporphyrin IX (PPIX). Thus, the accumulation of protoporphyrin IX (PPIX) is an indicator of inhibition of the heme biosynthesis and inhibition of the downstream enzyme.

Meanwhile, in the case where the function of upstream enzyme (ALAS2, ALAD, PBGD, URO3S, UROD, CPO) in the biosynthesis pathway is inhibited, the heme biosynthesis is blocked, but protoporphyrin IX (PPIX) does not accumulate.

The case of occurrence of strong heme biosynthesis inhibition induces anemia. If anemia is induced in a very critical period during embryonic development, there is a possibility of occurrence of fetal lethality, retarded fetal development, or teratogenicity such as ventricular septum defect accompanied by cardiac hypertrophy.

2. Method for Producing Cell Population Containing Embryonic Erythroblasts

The invention provides a method for producing a cell population containing embryonic erythroblasts. Hereinafter, this method is also referred to as the production method of the invention. The production method of the invention can give reproducible results even if the method is repeated multiple times. The production method according to an embodiment of the invention includes the steps of:

(1) subjecting pluripotent stem cells to suspension culture to form a cell aggregate;

(2) obtaining an embryonic erythroblast-containing cell population from the cell aggregate obtained in step (1).

<Step (1)>

The medium used in step (1) is not particularly limited as long as the medium is as described in the above definition section. The medium used in step (1) may be a serum-containing medium or a serum-free medium. A serum-free medium is preferably used from the viewpoint of avoiding contamination of chemically undefined components and preventing the component variation, due to the difference in the manufacturer and lot of serum, from affecting reproducibility. To avoid complicated preparation, it is preferable to use a commercially available stem cell medium, such as a mixed medium (manufactured by STEMCELL Technologies, Inc.) of STEMdiff Hematopoietic Basal Medium and STEMdiff Hematopoietic Supplement A. The medium used in step (1) also preferably contains a cytoprotective agent. The cytoprotective agent used at that time preferably contains a Rho-associated protein kinase (ROCK) inhibitor in order to suppress cell death and more preferably contains Y-27632. Step (1) is preferably carried out under conditions in the absence of growth factors such as erythropoietin, stem cell factor (SCF), interleukin-3 (IL-3), interleukin-11 (IL-11), hydrocortisone, or insulin-like growth factor (IGF), or feeder cells.

When step (1) is started, it is preferable that pluripotent stem cells cultured under undifferentiated state-maintaining conditions are dispersed into single cells. For this purpose, step (1) preferably follows an operation of dispersing pluripotent stem cells. The "dispersed cells" obtained by the dispersing operation are preferably single cells, but may contain, for instance, a cell mass including 2 to 100 cells, which is the small number, or a cell mass including 2 to 50 cells. The "dispersed cells" may contain, for instance, 70% or more of single cells and 30% or less of cell masses and preferably contain 80% or more of single cells and 20% or less of cell masses. The "dispersed cells" may refer to the state almost without any cell-to-cell attachment (e.g., plane attachment). In some embodiments, the "dispersed cells" may refer to the state almost without any cell-cell junction (e.g., adherence junction).

Examples of a procedure for dispersing pluripotent stem cells cultured under undifferentiated state-maintaining conditions include mechanical dispersing treatment, cell dispersing liquid treatment, or cytoprotective agent-adding treatment. These treatments may be combined. In this dispersing treatment, it is preferable that the cytoprotective agent-adding treatment and the cell dispersing liquid treatment may be performed at the same time, followed by the mechanical dispersing treatment. The dispersed cells are suspended in the above medium.

Examples of the mechanical dispersing treatment procedure include pipetting or scraping with a scraper.

Examples of the cell dispersing liquid used for the cell dispersing liquid treatment include a solution containing at least one of an enzyme (e.g., trypsin, collagenase, hyaluronidase, elastase, pronase, DNase, papain) or a chelator (e.g., ethylenediaminetetraacetic acid). It is also possible to use a commercially available cell dispersing liquid such as TripLE Select (manufactured by Thermo Fisher Scientific, Inc.), TripLE Express (manufactured by Thermo Fisher Scientific, Inc.), Accutase (manufactured by Innovative Cell Technologies, Inc.), or Accumax (manufactured by Innovative Cell Technologies, Inc.).

Examples of the cytoprotective agent used for the cytoprotective agent-adding treatment include an FGF signaling pathway-activating substance, heparin, a Rho-associated protein kinase (ROCK) inhibitor, a myosin inhibitor, or a serum substitute. Preferable examples of the cytoprotective agent include a ROCK inhibitor. A ROCK inhibitor may be added from the start of step (1) so as to suppress cell death of pluripotent stem cells (in particular, human pluripotent stem cells) induced by dispersing them. Examples of the ROCK inhibitor include Y-27632 ((R)-(+)-trans-4-(1-aminoethyl)-N-(4-pyridyl)cyclohexanecarboxamide, dihydrochloride), Fasudil (HA1077) (1-(5-Isoquinolinylsulfonyl)homopiperazine, hydrochloride), H-1152 (5-[[(2S)-hexahydro-2-methyl-1H-1,4-diazepin-1-yl]sulfonyl]-4-methyl-isoquinoline, dihydrochloride), or HA-1100 (Hydroxyfasudil) ([1-(1-hydroxy-5 soquinolinesulfonyl)homopiperazine, hydrochloride). The cytoprotective agent used may be a prepared cytoprotective agent. Examples of the prepared cytoprotective agent include RevitaCell Supplement (manufactured by Thermo Fisher Scientific, Inc.) or CloneR (manufactured by Stemcell Technologies, Inc.). These substances may be used singly or in combination.

Examples of the procedure for dispersing pluripotent stem cells include a process including: treating pluripotent stem cell colonies with a cell dispersing liquid (e.g., Accumax, Accutase) in the presence of a ROCK inhibitor as a cytoprotective agent; and further pipetting and dispersing the cells.

Dispersed pluripotent stem cells in suspension are seeded in cultureware; the dispersed pluripotent stem cells are subjected to suspension culture, that is, culture under conditions in which the cells are non-adherent to the cultureware. In this way, a plurality of pluripotent stem cells are assembled to form cell aggregates. For the suspension culture, it is preferable to use non-cell-adherent cultureware described above for the cultureware in step (1).

At this time, the dispersed pluripotent stem cells may be seeded on relatively large cultureware such as a 10-cm dish. Then, a plurality of cell aggregates may be formed at the same time in the one cultureware. However, from the viewpoint of causing a less variation in the size of each cell aggregate, a certain number of the dispersed pluripotent stem cells are preferably seeded on each well of a multi-well plate (with a U-shaped bottom or V-shaped bottom) like, for instance, a non-cell-adherent 96-well microplate. When these cells are subjected to static culture, they quickly assemble to form a single cell aggregate in each well. Examples of the multi-well plate include a PrimeSurface 96 V-bottom plate (MS-9096V; manufactured by Sumitomo Bakelite Co., Ltd.). If this cell aggregate is collected from multiple wells, a uniform cell aggregate population may be obtained. The uniform cell aggregates allow for more stabilization of production efficiency for each well and each replicated experiment, thereby more reproducibly producing an embryonic erythroblast-containing cell population.

The cell count of pluripotent stem cells seeded in step (1) may be set, if appropriate, to form cell aggregates more uniformly and efficiently. For instance, by using a 96-well microwell plate, human pluripotent stem cells may be subject to suspension culture. In this case, it is possible to add, to each well, a cell suspension prepared by including, per well, usually about $1 \times 10^2$ to about $1 \times 10^5$ cells, preferably about $5 \times 10^2$ to about $5 \times 10^4$ cells, more preferably about $1 \times 10^3$ to about $2 \times 10^4$ cells, still more preferably about $1.5 \times 10^3$ to about $1.6 \times 10^4$ cells, and particularly preferably about $2 \times 10^3$ to about $4 \times 10^3$ cells. Next, the plate is allowed to stand and cell aggregates are then formed. The cell count may be determined by counting the number using a hemocytometer.

The suspension culture period necessary for the formation of cell aggregates from dispersed pluripotent stem cells may be determined, if appropriate, depending on the pluripotent stem cells used. Here, it is desirable that the period is as short as possible in order to form uniform cell aggregates. During the formation of cell aggregates from dispersed cells, the cells assemble and the assembled cells then form cell aggregates. In the case of human pluripotent stem cells (e.g., human iPS cells), for instance, the cells assemble within preferably about 24 h, more preferably within about 12 h, and still more preferably within 6 h from the timepoint of seeding dispersed cells (i.e., the start of suspension culture). Then, cell aggregates are formed within preferably about 72 h, more preferably within about 48 h, and still more preferably within 24 h. The time to form the aggregates may be controlled, if appropriate, by using cell aggregation tools and/or adjusting centrifugation conditions.

In the production method of the invention, it is preferable that dispersed pluripotent stem cells are made to quickly assemble to form uniform cell aggregates. Examples of an experimental operation of assembling cells include a procedure for trapping cells in a small space by using, for instance, a small-well plate (e.g., a plate with a well bottom area of about 0.1 to 2.0 $cm^2$ in terms of flat bottom area) or a micropore; or a procedure for assembling cells by short-term centrifugation using a small centrifuge tube. Examples of the small-well plate include a 24-well plate (with an area of about 1.88 $cm^2$ in terms of flat bottom area), a 48-well plate (with an area of about 1.0 $cm^2$ in terms of flat bottom area), a 96-well plate (with an area of about 0.35 $cm^2$ in terms of flat bottom area and an inner diameter of about from 6 to 8 mm), or a 384-well plate. Preferable examples include a 96-well plate. As the shape of the small-well plate, the bottom shape when the well is viewed from the top include a polygon, rectangle, ellipse, or perfect circle. Preferred is a perfect circle. As the shape of the small-well plate, examples of the bottom shape when the well is viewed from the side include a U-shaped bottom, V-shaped bottom, or M-shaped bottom because of the structure having a high circumference portion and a low inner recess portion. Preferred is a U-shaped bottom or V-shaped bottom. Most preferred is a V-shaped bottom. It is also possible to use, as the small-well plate, a cell culture dish (e.g., a 60-mm to 150-mm dish or culture flask) having roughness or an indent at the bottom. The bottom surface of the small-well plate is a non-cell-adherent bottom surface and preferably a bottom surface having a non-cell-adherent coating.

In step (1), it is preferable that pluripotent stem cells are seeded on cultureware, and the cells are then assembled by centrifugation to promote the formation of cell aggregates. The centrifugation conditions may be suitably set. For instance, a swing rotor-equipped plate centrifuge may be used to perform centrifugation for 1 min to 10 min at a centrifugal acceleration of from 100 G to 300 G. This can promote the formation of cell aggregates.

The culture conditions such as the culture temperature and $CO_2$ concentration during step (1) may be set, if appropriate. The culture temperature is, for instance, from about 30° C. to about 40° C. and preferably about 37° C. The $CO_2$ concentration is, for instance, from about 1% to about 10% and preferably about 5%.

It is possible to determine whether cell aggregates are formed, based on, for instance, the size and cell count of each cell aggregate, macroscopic morphology, and/or microscopic morphology and its uniformity by histological staining analysis, expression of differentiation and undifferentiation markers and their uniformity, regulation of differentiation marker expression and its synchronization, and/or reproducibility of differentiation efficiency among aggregates.

After cell aggregates are formed, the cell aggregates may be continuously cultured as they are in order to obtain desired cell aggregates. The total period of the suspension culture period in step (1), that is, the time to assemble the above cells, the time to form cell aggregates, and the optionally continued suspension culture period are usually 8 h or more and about 6 days or less and preferably 12 h or more and about 96 h or less. Specifically, it is preferable that the time from the start of step (1) to the start of step (2a) described later is preferably 12 h or more and about 96 h or less. Too short culture period tends to cause a smaller number of cells included in each cell aggregate. Too long culture period tends to cause excessive progression of cellular differentiation.

<Step (2)>

Step (2) is a step of obtaining an embryonic erythroblast-containing cell population from the cell aggregate obtained in step (1).

The embryonic erythroblast-containing cell population may be any cell population as long as embryonic erythroblasts are contained, may contain all the cells derived from cell aggregates, or may be part of cell population including all the cells. The cell population is a cell population preferably existing in an environment different from an environment where embryonic erythroblasts are present in vivo or preferably having component cell types or a cell abundance ratio different from a cell population in an environment where embryonic erythroblasts are present in vivo.

The cell population obtained in step (2) contains embryonic erythroblasts. The embryonic erythroblasts are cells described in the above definition section. The embryonic erythroblasts are identified by immunostaining against ε-globin. The gene expression and functions of embryonic erythroblasts included in the cell population are assumed to be substantially the same as of in vivo embryonic erythroblasts.

The results of immunostaining can be interpreted by the procedure well-known to those skilled in the art, such as visual assessment by those skilled in the art or quantitative analysis using image-analyzing software for an captured image. One can consult, for instance, "Protein, Nucleic Acid and Enzyme", Vol. 54, No. 2 (2009) P 185-192 to interpret the results of immunostaining. Here, false positive caused by, for instance, autofluorescence, non-specific adsorption of secondary antibody, or leakage of fluorescence during multiple staining should be eliminated. The presence or absence of expression of ε-globin was determined according to the protocol designated in the below-described preliminary experiment.

The embryonic erythroblast-containing cell population refers to any cell population, and preferably at least 70% and more preferably at least of 80% of cells among the cells included in the cell population are embryonic erythroblasts. The production method of the invention makes it possible to obtain a number of embryonic erythroblasts, so that the percentage of embryonic erythroblasts included in the population can be made larger. The percentage of embryonic erythroblasts in the cell population with respect to viable cells observed by nuclear staining can be determined as the number of cells recognized as expressing ε-globin by substantially the same protocol for immunostaining in the below-described preliminary experiment.

In addition, preferably at least 50% and more preferably at least 60% of β-globin gene family expressed in cells of the cell population is ε-globin gene. The production method of the invention makes it possible to obtain a cell population having increased expression of ε-globin. The percentage of expression of ε-globin gene among the β-globin gene family can be calculated as the relative expression level of ε-globin gene mRNA with respect to the total level of β-globin gene family mRNA. The relative expression level of mRNA can be calculated by substantially the same protocol as for real-time PCR in Example 1 described below.

<Step (2a)>

Step (2) includes step (2a) of subjecting the cell aggregate to adhesion culture.

The medium used in step (2a) is not particularly limited as long as the medium is as described in the above definition section. The medium used in step (2a) may be a serum-containing medium or a serum-free medium. A serum-free medium is preferably used in the invention from the viewpoint of avoiding contamination of chemically undefined components and preventing the component variation, due to the difference in the manufacturer and lot of serum, from affecting reproducibility. To avoid complicated preparation, it is preferable to use a commercially available stem cell medium, such as a mixed medium (manufactured by STEMCELL Technologies, Inc.) of STEMdiff Hematopoietic Basal Medium and STEMdiff Hematopoietic Supplement B. The medium used in step (2a) also preferably contains a cytoprotective agent so as to suppress cell death of pluripotent stem cells. The cytoprotective agent used at that time is preferably the same agent as used in step (1), more preferably includes a ROCK inhibitor, and still more preferably includes Y-27632.

Step (2a) is preferably performed using cell-adherent cultureware. The cell-adherent cultureware is not particularly limited if surface treatment or the like allowing for the above cell attachment is implemented. Examples of such cultureware that can be used include a commercially available 3.5-cm dish, 6-cm dish, or 10-cm dish for adherent cell culture or a cell culture plate such as a 24-well plate or 6-well plate.

From the viewpoint of promoting adhesion of cell aggregates and differentiation into erythroblasts, the cultureware used in step (2a) is preferably coated with a cell adhesion/attachment-promoting matrix. Examples of the above matrix include a synthetic matrix such as a basement membrane preparation, recombinant extracellular matrix, poly-D-lysine, poly-L-lysine, poly-L-ornithine, or Synthemax. The cell adhesion/attachment-promoting matrix used in the invention preferably includes a basement membrane preparation and more preferably includes Matrigel.

The adhesion culture in step (2a) is carried out by transferring the cell aggregates formed in step (1) to cell-adherent cultureware. The transferring procedure used at that time is not particularly limited, and it is preferable that a physical load onto the cell aggregates is less. Examples of such a transferring procedure include aggregate transfer using a wide-bore pipet tip and a micropipette.

Step (2a) may be carried out in the presence of feeder cells. The feeder cells are not particularly limited, and are preferably bone marrow stromal cells, a bone marrow stromal cell-derived cell line, or fibroblasts, preferably OP9 cells (mouse bone marrow stromal cells) or C3H10T1/2 cells (clone 8) (mouse embryonic fibroblasts), and more preferably OP9 cells. The cell aggregates may be subject to adhesion culture on the feeder cells seeded to promote differentiation into embryonic erythroblasts. In the case of using, in particular, rat ES cells as the pluripotent stem cells, the efficiency of differentiation into embryonic erythroblasts can be improved more.

Step (2a) is preferably performed in the presence of at least one selected from the group consisting of erythropoietin, erythropoietin receptor-activating substances, and erythropoietin receptor-mediated signaling pathway-activating substances. Examples of the erythropoietin receptor-activating substances include darbepoetin, methoxy polyethylene glycol-epoetin beta, or erythropoietin mimetic peptides. Examples of the erythropoietin receptor-mediated signaling pathway-activating substances include Janus kinase 2 (JAK2) activators or JAK2 phosphatase inhibitors. The concentration of the above substance may be set, if appropriate. From the viewpoint of efficiency of differentiation into embryonic erythroblasts, the concentration in the presence of erythropoietin in step (2a) is, for instance, 1 ng/mL or more and 500 ng/mL or less and preferably 10 ng/mL or more and 100 ng/mL or less. When a substance other than erythropoietin is used, it is preferable to use the concentration that can exert substantially the same effects of the signaling pathway as of erythropoietin at the above concentration. In addition, the addition timing of these factors may be the same as or different from the start of step (2a).

Meanwhile, from the viewpoint of making efficient differentiation into embryonic erythroblasts, step (2a) may be performed in the presence of an additional growth factor(s) or the like, and is preferably performed in the presence of at least one selected from the group consisting of stem cell factor (SCF), interleukin 3 (IL-3), interleukin 11 (IL-11), hydrocortisone, and insulin-like growth factor (IGF). The concentration of each factor may be set, if appropriate. The concentration in the presence of stem cell factor in step (2a) is, for instance, 1 ng/mL or more and 500 ng/mL or less and preferably 10 ng/mL or more and 100 ng/mL or less. The concentration in the presence of interleukin 3 in step (2a) is, for instance, 0.1 ng/mL or more and 100 ng/mL or less and preferably 1 ng/mL or more and 50 ng/mL or less. The concentration in the presence of interleukin 11 in step (2a) is, for instance, 0.1 ng/mL or more and 100 ng/mL or less and preferably 1 ng/mL or more and 50 ng/mL or less. The concentration in the presence of hydrocortisone in step (2a) is, for instance, 0.01 μM or more and 50 μM or less and preferably 0.1 μM or more and 10 μM or less. The concentration in the presence of insulin-like growth factor in step (2a) is, for instance, 0.1 ng/mL or more and 100 ng/mL or less and preferably 1 ng/mL or more and 50 ng/mL or less. In addition, the addition timing of these factors may be the same as or different from the start of step (2a).

The culture conditions such as the culture temperature and $CO_2$ concentration during step (2a) may be set, if appropriate. The culture temperature is, for instance, from about 30° C. to about 40° C. and preferably about 37° C. The $CO_2$ concentration is, for instance, from about 1% to about 10% and preferably about 5%.

The culture period of step (2a) may be set, if appropriate, depending on the types of cells and/or the culture conditions, until a cell population of interest is obtained. In the case of using human iPS cells, the period is, for instance, 2 days or more and 18 days or less, preferably 3 days or more and 18 days or less, and more preferably 4 days or more and 10 days or less. In the case of using rat ES cells, the period is, for instance, 2 days or more and 18 days or less, preferably 2 days or more and 10 days or less, and more preferably 3 days or more and 8 days or less. Too short culture period is unlikely to produce embryonic erythroblasts. Too long culture period tends to cause excessive differentiation of embryonic erythroblasts <Step (2b)>

Step (2) may further include step (2b) of collecting the embryonic erythroblast-containing cell population.

The cell population collected in step (2b) may be at least one kind selected from the group consisting of adherent cells and floating cells obtained after the culture in step (2a). From the viewpoint of increasing the percentage of embryonic erythroblasts in the cell population, it is preferable to collect only the floating cells. Collection of only the floating cells makes it easier to obtain a cell population in which preferably at least 70% and more preferably at least 80% of cells among the cells included in the cell population are embryonic erythroblasts. In addition, the collection of only the floating cells also makes it easier to obtain a cell population in which preferably at least 50% and more preferably at least 60% of β-globin gene family expressed in the cells is ε-globin gene. The floating cells collected may be all or part of the floating cells.

The procedure for collecting floating cells is not particularly limited, and may be a procedure for recovering a floating cell-containing medium into, for instance, a tube by a pipet or the like. The tube or the like may be centrifuged to remove supernatant so as to yield a cell population pellet. Examples of another procedure for collecting floating cells include fluorescence activated cell sorting (FACS) using an antibody against a cell surface marker, magnetic cell separation (MACS), or filtration.

Step (2b) may be performed in the presence of a cytoprotective agent for stabilization of cells. The cytoprotective agent used at that time preferably includes a ROCK inhibitor, and more preferably includes Y-27632.

<Step (3)>

It is possible to include step (3) of further culturing the embryonic erythroblast-containing cell population obtained in step (2).

The cell population cultured in step (3) is preferably the cell population collected in step (2b), more preferably the embryonic erythroblast-containing cell population obtained by collecting floating cells in step (2b). In step (3), suspension culture is preferably performed using cell-adherent cultureware. Since cell-adherent cultureware is used to subject a cell population to suspension culture, adherent cells other than erythroblasts can be attached to cultureware and the adherent cells can be removed from a floating cell population. In addition, step (3) is preferably performed in the absence of feeder cells.

The medium used in step (3) may be the same as or different from the medium used in the above step (2a). In step (3), it is preferable to use, for instance, a commercially available mixed medium (manufactured by STEMCELL Technologies, Inc.) of STEMdiff Hematopoietic Basal Medium and STEMdiff Hematopoietic Supplement B in the case of using human iPS cells; and it is preferable to use Stemline II medium (manufactured by Sigma-Aldrich Co. LLC) in the case of using rat ES cells. The medium used in step (3) may contain a cytoprotective agent for stabilization of cells, preferably contains a ROCK inhibitor, and more preferably contains Y-27632.

Step (3) is preferably performed in the presence of at least one selected from the group consisting of erythropoietin, erythropoietin receptor-activating substances, and erythropoietin receptor-mediated signaling pathway-activating substances. These factors may be the factors that have been used in the above step (2a) and continue to be used. The concentration of each factor may be the same as or different from the concentration used in the above step (2a). The concentration in the presence of erythropoietin in step (3) is, for instance, 1 ng/mL or more and 500 ng/mL or less and preferably 10 ng/mL or more and 100 ng/mL or less. When a substance other than erythropoietin is used, it is preferable to use the concentration that can exert substantially the same effects of the signaling pathway as of erythropoietin at the above concentration. In addition, step (3) may be performed in the presence of stem cell factor. The concentration of stem cell factor used may be the same as or different from the concentration used in the above (2a). The addition timing of these factors may be the same as or different from the start of step (3).

Meanwhile, step (3) is preferably free of at least one selected from the group consisting of interleukin 3, interleukin 11, hydrocortisone, and insulin-like growth factor. It is more preferable that neither interleukin 3, interleukin 11, hydrocortisone, nor insulin-like growth factor is included. In addition, step (3) is preferably performed under conditions without any feeder cells. It has been known that when an embryonic erythroblast-containing cell population is continuously cultured under differentiation-inducing conditions, the level of expression of ε-globin, an embryonic erythroblast marker, decreases while the levels of expression of γ-globin and β-globin increase, so that the cell population is progressively differentiated into fetal or adult erythroblasts. However, if step (3) is performed under the above conditions, the percentage of ε-globin-expressing embryonic erythroblasts among cells included in the cell population can be kept high even when the culture continues. In addition, the level of expression of ε-globin among the β-globin gene family expressed in the cells of the population can also be kept high.

The culture conditions such as the culture temperature and $CO_2$ concentration during step (3) may be set, if appropriate. The culture temperature is, for instance, from about 30° C. to about 40° C. and preferably about 37° C. The $CO_2$ concentration is, for instance, from about 1% to about 10% and preferably about 5%.

The culture period of step (3) may be set, if appropriate, depending on the types of cells and/or the culture conditions, so as to obtain a cell population of interest. For instance, the period may be set to 2 days or more. In the case of using human iPS cells, the period may be 4 days or more, or 8 days or more and 14 days or less. In the case of using rat ES cells, the period may be 3 days or more, or 4 days or more and 10 days or less.

The pluripotent stem cells used in the production method of the invention are not particularly limited and are preferably ES cells or iPS cells. The pluripotent stem cells used in the production method of the invention are preferably mammalian pluripotent stem cells, more preferably primate pluripotent stem cells, rodent pluripotent stem cells, or rabbit pluripotent stem cells, and still more preferably human pluripotent stem cells or rat pluripotent stem cells.

3. Compound Test Method Using Cell Population Containing Embryonic Erythroblasts The compound test method using a cell population containing embryonic erythroblasts includes:

(A) subjecting pluripotent stem cells to suspension culture to form a cell aggregate;

(B) obtaining an embryonic erythroblast-containing cell population from the cell aggregate obtained in step (A);

(C) culturing the cell population in the presence of a test compound; and (D) measuring at least one metric selected from 1) a cell count, 2) heme concentration, 3) a protoporphyrin IX concentration, or 4) a globin expression level of the embryonic erythroblast-containing cell population cultured in step (C).

<Step (A)>

Step (A) may be performed using the same procedure as in step (1) of the above [2. Method for Producing Cell Population Containing Embryonic Erythroblasts].

<Step (B)>

Step (B) may be performed using the same procedure as in step (2) of the above [2. Method for Producing Cell Population Containing Embryonic Erythroblasts]. Step (B) includes step (Ba) of subjecting the cell aggregate to adhesion culture. Step (Ba) may be performed using the same procedure as in step (2a) of the above [2. Method for Producing Cell Population Containing Embryonic Erythroblasts]. In addition, step (B) may further include step (Bb) of collecting the cell population. Step (Bb) may be performed using the same procedure as in step (2b) of the above [2. Method for Producing Cell Population Containing Embryonic Erythroblasts].

<Step (C)>

In step (C), the cell population obtained in step (B) is cultured in the presence of a test compound. The cell population cultured in step (C) is preferably the cell population collected in step (Bb) and more preferably the cell population obtained by collecting floating cells in step (Bb).

Unless otherwise indicated, for instance, the medium, growth factors, cultureware, and other culture conditions used in step (C) are preferably the same as in step (3) of the above [2. Method for Producing Cell Population Containing Embryonic Erythroblasts]. In step (C), it is preferable that suspension culture is preferably performed using cell-adherent cultureware. In addition, step (C) is preferably performed in the absence of feeder cells.

The test compound used in step (C) is not particularly limited and is preferably a substance that inhibits hemoglobin synthesis, inhibits normal fetal development, or induces teratogenicity or embryonic lethality or a substance suspected of being so. Examples of the test compound include dihydroartemisinin or succinylacetone. The concentration of the test compound may be set, if appropriate, to be within a suitable range for a test. A test compound control used may be a solvent used for solubilizing the test compound. Examples include dimethylsulfoxide (DMSO). However, a test compound-free condition may be used.

The procedure for culturing a cell population in the presence of a test compound is not particularly limited as long as in the procedure, cells included in the cell population are in contact with the test compound. Examples include a procedure in which a test compound is added to a medium used for culturing a cell population; or a procedure in which culturing of a cell population is started in a medium to which a test compound has been added.

In the present method, preferably at least 70% and more preferably at least 80% of cells among the cells included in the cell population are embryonic erythroblasts. That is, expression of ε-globin, an embryonic erythroblast marker, is preferably kept in 70% or more of cells in the cell population until the cell population is obtained in (B), cultured in step (C), and analyzed in step (D). The percentage of embryonic erythroblasts in the cell population with respect to viable cells observed by nuclear staining can be determined as the number of cells recognized as expressing ε-globin by substantially the same protocol of immunostaining in the below-described preliminary experiment. If the percentage of embryonic erythroblasts in the cell population is within the above range, the effects of the compound on the embryonic erythroblasts can be more suitably investigated.

In addition, it is preferable in the invention that preferably at least 50% and more preferably at least 60% of β-globin gene family expressed in cells of the cell population is ε-globin gene. Specifically, at least 50% and more preferably at least 60% of β-globin gene family expressed in cells of the cell population is ε-globin gene expressed until the cell population is obtained in step (B), cultured in step (C), and analyzed in step (D). The percentage of expression of ε-globin gene among the β-globin gene family can be calculated as the relative expression level of ε-globin gene mRNA with respect to the total level of β-globin gene family mRNA. The relative expression level of mRNA can be calculated by substantially the same protocol as for real-time PCR in Example 1 described below. If the relative expression level of ε-globin gene mRNA with respect to the total level of β-globin gene family mRNA is within the above range, the effects of the compound on the embryonic erythroblasts can be more accurately investigated.

Step (C) is preferably free of at least one selected from the group consisting of interleukin 3, interleukin 11, hydrocortisone, and insulin-like growth factor. It is more preferable that neither interleukin 3, interleukin 11, hydrocortisone, nor insulin-like growth factor is included. In addition, step (C) is preferably performed under conditions without any feeder cells. It has been known that when an embryonic erythroblast-containing cell population is continuously cultured under differentiation-inducing conditions, the level of expression of ε-globin, an embryonic erythroblast marker, decreases while the levels of expression of γ-globin and β-globin increase, so that the cell population is progressively differentiated into fetal or adult erythroblasts. However, if step (C) is performed under the above conditions, the percentage of ε-globin-expressing embryonic erythroblasts among cells included in the cell population can be kept high even when the culture continues. In addition, the level of expression of ε-globin among the β-globin gene family expressed in the cells of the population can also be kept high. This enables the effects on the embryonic erythroblasts, in particular, to be examined even in the case where culturing for several days is desirable to examine the effects of the compound.

The culture period of step (C) may be set, if appropriate, depending on the types of cells and/or the culture conditions. For instance, the period may be set to 2 days or more. In the case of using human iPS cells, the period may be 4 days or more, or 8 days or more and 14 days or less. In the case of using rat ES cells, the period may be 3 days or more, or 4 days or more and 10 days or less.

<Step (D)>

Step (D) includes measuring at least one metric selected from the group consisting of 1) the cell count, 2) the cell viability, 3) the heme concentration, 4) the protoporphyrin IX concentration, and 5) the globin expression level of the cell population cultured in step (C). The above metric measurement results may be used and the above metrics of the cell population undergoing step (C) in the presence of a control (e.g., a solvent control such as DMSO) may be measured to examine the effects of the test compound on the embryonic erythroblasts. In addition, a plurality of test compounds including a control compound may be used to measure the above metrics of the cell population undergoing step (C) in the presence of each test compound, and the results are then compared. This also enables screening for a test compound that can inhibit hemoglobin synthesis, inhibit normal fetal development, or induce teratogenicity or embryonic lethality.

1) Cell Count and 2) Cell Viability

The cell count may be calculated by counting viable cells in the cell population after cultured in step (C) by using, for instance, a hemocytometer or automatic cell counter. The cell viability may be measured, if appropriate, by a protocol such as the method using Trypan blue dye to stain dead cells, the intracellular ATP quantification, MTT assay using mitochondrial activity, or viable cell esterase activity measurement using, for instance, calcein AM. For instance, in the method using Trypan blue dye, the number of Trypan blue-negative cells at the end of culturing in step (C) is divided by the total of the number of Trypan blue-negative cells and the number of positive cells to give a value of interest.

3) Heme Concentration and 4) Protoporphyrin IX Concentration

The heme concentration or the protoporphyrin IX concentration may be measured by analysis, such as liquid chromatography-mass spectrometry (LC-MS), of the cell population.

5) Globin Expression Level

The globin expression level may be measured by a known method for detecting the level of expression of RNA or protein. The globin RNA expression level may be measured by, for instance, extracting RNA from the cell population by a known procedure and then by, for instance, real-time PCR or transcriptome analysis. The globin protein expression level may be measured by, for instance, extracting proteins from the cell population by a known procedure and then by, for instance, Western blot, enzyme-linked immunoabsorbent assay (ELISA), or liquid chromatography-mass spectrometry (LC-MS).

In addition to the above 1) to 5) metrics, the level(s) of expression of differentiation marker gene(s) may be measured to examine the effects on cellular differentiation. The above metrics may be measured by, for instance, metabolomics analysis, exome analysis, or epigenome change analysis other than the exemplified procedures to examine the effects of the test compound on the embryonic erythroblast-containing cell population.

The pluripotent stem cells used in the test method of the invention are not particularly limited and are preferably ES cells or iPS cells. The pluripotent stem cells used in the test method of the invention are preferably mammalian pluripotent stem cells, more preferably primate pluripotent stem cells, rodent pluripotent stem cells, or rabbit pluripotent stem cells, and still more preferably human pluripotent stem cells or rat pluripotent stem cells.

<Compound Test Method Using Cell Population Containing Embryonic Erythroblasts Derived from Each of Plurality of Biological Species>

The above compound test method may be performed using a cell population containing embryonic erythroblasts derived from each of a plurality of biological species. In step (D), the cell population obtained from pluripotent stem cells derived from each of a plurality of biological species may be used for the measurement. The cell population obtained from pluripotent stem cells derived from each of a plurality of biological species may be subjected to the above measurement. The results may then be compared to check the difference in the effects of the test compound between each cell population.

The plurality of biological species are preferably mammals, more preferably include at least two biological species selected from the group consisting of primates, rodents, and Lagomorpha, and still more preferably include a human and a rat.

4. Cell Population Containing Embryonic Erythroblasts

In cells included in the embryonic erythroblast-containing cell population in the invention, at least 70% of the cells are embryonic erythroblasts, and preferably at least 80%, more preferably at least 90%, still more preferably at least 95%, and most preferably at least 99% of the cells are embryonic erythroblasts.

The embryonic erythroblast-containing cell population may be produced like in the procedure described in the above [2. Method for Producing Cell Population Containing Embryonic Erythroblasts]. Here, a floating cell population among them may be collected to yield a cell population in which at least 70% or 80% of the cells are embryonic erythroblasts. The floating cell population may be, for instance, further sorted by FACS or MACS to collect ε-globin-expressing cells. This makes it possible to obtain a cell population in which at least 90% of the cells are embryonic erythroblasts.

The embryonic erythroblast-containing cell population may be a cell population used for a compound test. Examples of the compound test include the test described in the above [3. Compound Test Method Using Cell Population Containing Embryonic Erythroblasts].

The embryonic erythroblast-containing cell population is preferably stored while expression of ε-globin is maintained. The storage involves that the cell population is, for instance, placed while being able to be transferred. In addition, the state where expression of ε-globin is maintained refers to the state where the amount of change in the percentage of embryonic erythroblasts in the cell population or the level of expression of ε-globin among the β-globin gene family in the cell population between before and after the storage is, for instance, within 30% and preferably within 20%.

Examples of such storage conditions include conditions in which the cell population is stored in, for instance, a medium, saline, or a storage solution without contact with feeder cells or feeder cell supernatant, or at least one selected from the group consisting of, for instance, interleukin 3, interleukin 11, hydrocortisone, and insulin-like growth factor. In addition, the storage may be carried out under freezing conditions (at less than 0° C.), under low-temperature conditions (at, for instance, 0° C. or more and less than 25° C.), or under conditions close to the culture temperature (at 25° C. or more and 38° C. or less). Under the freezing conditions, for instance, the cell population may be suspended in a cell cryopreservation solution, dispensed into a cryotube(s), and cryo-preserved at an ultra-low temperature (at from −150° C. to −70° C.) or in liquid nitrogen (at −196° C.).

The cell population may be preserved while expression of ε-globin is maintained. This case allows for culturing of a cell population with an increased percentage of embryonic erythroblasts when the cell population is, for instance, further cultured.

5. Cell Culture Composition

The cell culture composition includes an embryonic erythroblast-containing cell population and a medium. The embryonic erythroblast-containing cell population may be produced like in the procedure described in the above [2. Method for Producing Cell Population Containing Embryonic Erythroblasts]. The cell culture composition may be a suspension in which the cell population is suspended in the medium, or the cell population may be separated from the medium.

The medium may be a medium used in step (C) of the above [3. Compound Test Method Using Cell Population Containing Embryonic Erythroblasts].

The medium included in the cell culture composition is preferably free of at least one selected from the group consisting of interleukin 3, interleukin 11, hydrocortisone, and insulin-like growth factor. It is more preferable that neither interleukin 3, interleukin 11, hydrocortisone, nor insulin-like growth factor is included. In addition, the medium included in the cell culture composition is preferably free of feeder cell culture supernatant.

Further, the medium included in the cell culture composition preferably contains at least one selected from the group consisting of erythropoietin, erythropoietin receptor-activating substances, and erythropoietin receptor-mediated signaling pathway-activating substances. Furthermore, the medium included in the cell culture composition optionally contains stem cell factor.

EXAMPLES

Hereinbelow, the invention will be described in more detail with reference to Examples. However, these Examples do not restrict the scope of the invention. In addition, unless otherwise limited, reagents and materials used are commercially available.

[Preliminary Experiment: Quantification and Criteria of Immunostaining Results]

Figure 2:
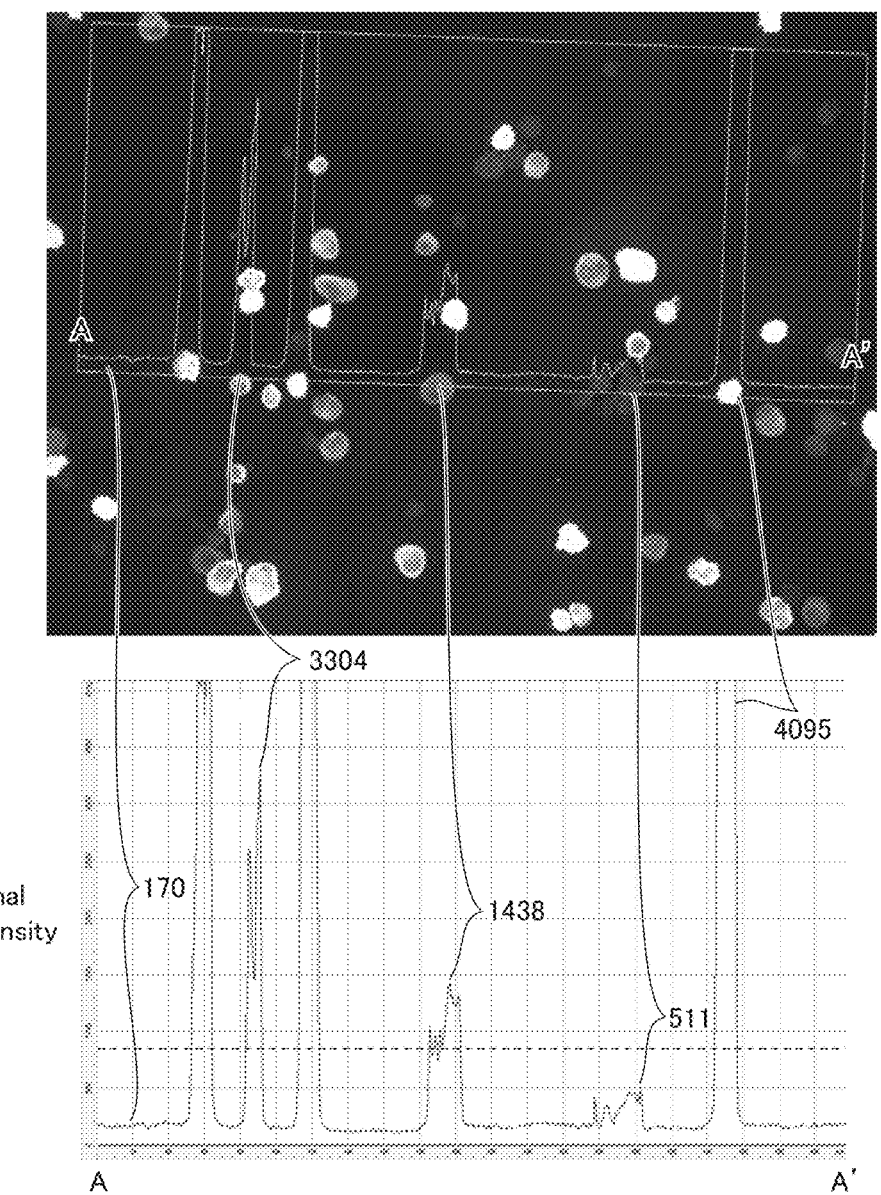
In FIG. 2, the upper panel shows the results of fluorescent immunostaining with an anti-HBE1 antibody while a cell population at Day 10 after the start of suspension culture (step (1)) was used in a preliminary experiment; and the lower panel is a graph in which the linear fluorescent intensity profile of an area of interest indicated by line A-A' of the upper panel was output.

To determine whether fluorescent immunostaining samples were positive or negative, the fluorescent intensities were quantified. For the staining intensity quantification technique, fluorescent immunostaining using an anti-HBE1 antibody was performed, by substantially the same protocol as in Example 1, on a smear sample of floating cell population at Day 10 after the start of suspension culture (step (1)) as produced in Example 1. The linear fluorescent intensity profile of an area of interest indicated by line A-A' was output to the resulting captured image (the upper panel of FIG. 2) (obtained at a maximum excitation wavelength of 490 nm and a maximum fluorescence wavelength of 525 nm). Then, the fluorescent intensities between a cell-containing region and a cell-free region were compared. The analysis results shown in the lower panel of FIG. 2 demonstrated that the fluorescent intensity of a cell-free region was 170; the numerical value for a region that had a strong fluorescent intensity and was visually determined as positive was 4095; and the numerical value for a positive region that had a weaker fluorescent intensity than the above was 1438. By contrast, the numerical value for a region that was visually determined as negative was 511. Thus, as indicated by a dashed line of the graph in the lower panel of FIG. 2, whether the antigen staining results were determined as positive or negative was found to be able to be quantitatively determined by defining, as positive, a site that exhibited the numerical value 5 times or more than the average of fluorescent intensities of regions identified as cell-free in the bright visual field. In the experiments below, substantially the same protocol as in this preliminary experiment was used to determine whether the expression was positive or negative.

Example 1: Embryonic Erythroblast-Containing Cell Population Produced from Human iPS Cells <Maintenance Culture>

Human iPS cells (HC-6 #10 strain; obtained from RIKEN, Japan) were subject to maintenance culture under feeder-free conditions in accordance with the protocol described in Scientific Reports, 4, 3594 (2014). The feeder-free medium used was StemFit AK02N medium (manufactured by AJINOMOTO CO., INC.) (hereinafter, referred to as "StemFit medium"). The feeder-free scaffold used was Laminin 511-E8 (manufactured by Nippi, Inc.).

The specific maintenance culture operation includes: first washing sub-confluent human iPS cells with PBS; performing enzymatic treatment with Accumax (manufactured by Innovative Cell Technologies, Inc.); then scraping the cells off the surface of a culture dish by adding StemFit medium and using a cell scraper; and pipetting and dispersing the cells into single cells. After that, the human iPS cells, which had been dispersed into single cells, were seeded on a plastic culture dish coated with Laminin 511-E8 under conditions at 0.5 μg/cm$^2$, and were then subjected to feeder-free culture in StemFit medium in the presence of Y27632 (a ROCK inhibitor, manufactured by Wako Pure Chemical Industries, Ltd., at 10 μM). In the case of using, as the plastic culture dish, a 6-well plate (with a culture area of 9.5 cm$^2$; for cell culture; manufactured by Corning, Inc.), the number of seeded human iPS cells, which had been dispersed into single cells, was 1.4×10$^4$. The whole volume of the media was changed to Y27632-free StemFit medium at Day 1 after the seeding. Then, the whole volume of the media was changed to Y27632-free StemFit medium once every 1 to 2 days. After that, the culture continued until the cells became sub-confluent (to the extent to which 60% of the culture area was covered by the cells) at Day 7 after the seeding.

<Step (1)>

Figure 3:
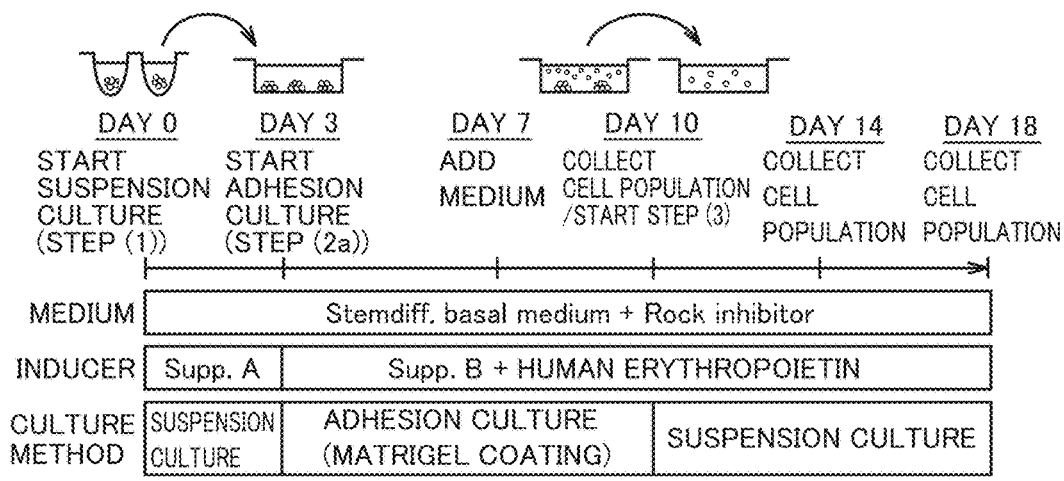
FIG. 3 is a diagram schematically illustrating a procedure when an embryonic erythroblast-containing cell population was produced from human iPS cells (HC-6 #10 strain) in Example 1. The days in the diagram each indicate the number of days after the start of step (1).

According to the procedure illustrated in FIG. 3, differentiation of human iPS cells was started to be induced. Sub-confluent human iPS cells prepared were washed with PBS; enzymatic treatment with Accumax was performed; the cells were then scraped off the surface of a culture dish by adding StemFit medium and using a cell scraper; and the cells were pipetted and dispersed into single cells. The resulting human iPS cell-containing suspension was centrifuged to remove the medium. The human iPS cells were resuspended in a mixed medium (manufactured by STEMCELL Technologies, Inc.) of STEMdiff Hematopoietic Basal Medium and STEMdiff Hematopoietic Supplement A (hereinafter, referred to as "STEMdiff+A medium"), and were seeded at 3×10$^3$ cells in 75 μL of medium per well of a non-cell-adherent 96-well culture plate (PrimeSurface 96-well V-bottom plate; manufactured by Sumitomo Bakelite Co., Ltd.) in the presence of Y27632 (at a final concentration of 20 μM).

The culture plate was centrifuged for 5 min at 1000 rpm in a centrifuge (CF8DL, manufactured by Koki Holdings Co., Ltd.), and the cells were subjected to suspension culture under conditions at 37° C. and 5% $CO_2$ (step (1) was started).

<Step (2)>

Figure 4:
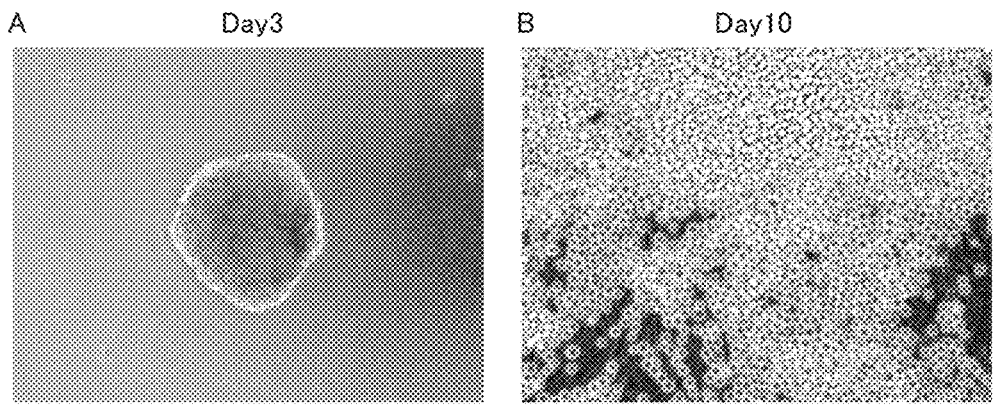
FIG. 4A is a bright-field image, observed under an inverted microscope, of a cell aggregate derived from human iPS cells (HC-6 #10 strain) at Day 3 after the start of suspension culture (step (1)) in Example 1.
FIG. 4B is a bright-field image, observed under an inverted microscope, of a floating embryonic erythroblast-containing cell population derived from human iPS cells (HC-6 #10 strain) at Day 10 after the start of suspension culture (step (1)).

The resulting 5 pieces of cell aggregate derived from the human iPS cells at Day 3 after the start of suspension culture (step (1)) were transferred, using a micropipette, per well of a cell-adherent 6-well plate coated with growth factor-reduced Matrigel (manufactured by Corning, Inc.) diluted 20-fold, and were subjected to adhesion culture under conditions at 37° C. and 5% $CO_2$ (step (2a) was started). The media used at that time was 1 mL per well of a mixed medium (manufactured by STEMCELL Technologies, Inc.) of STEMdiff Hematopoietic Basal Medium and STEMdiff Hematopoietic Supplement B further supplemented with human recombinant erythropoietin (at a final concentration of 30 ng/mL, manufactured by GenScript, Inc.) and Y27632 (at a final concentration of 20 μM) (hereinafter, referred to as "STEMdiff+B medium") How a cell aggregate looked from the start of suspension culture (step (1)) to Day 3 (immediately after the start of step (2a)) was observed in the bright field with an inverted microscope (BIOREVO; manufactured by KEYENCE CORPORATION) (FIG. 4A).

At Day 7 (Day 4 after the start of step (2a)) after the start of suspension culture (step (1)), 0.5 mL of the STEMdiff+B medium was further added. A floating cell population in the medium appeared and was observed (FIG. 4B) in the bright field with an inverted microscope at Day 10 (Day 7 after the start of step (2a)) after the start of suspension culture (step (1)).

At Day 10 (Day 7 after the start of step (2a)) after the start of suspension culture (step (1)), the floating cell population-containing medium was collected (step (2b)), and then centrifuged for 3 min at 7500 rpm in a centrifuge (centrifuge 5424; manufactured by Eppendorf, Inc.) to remove the supernatant.

<Step (3)>

At Day 10 (Day 7 after the start of step (2a)) after the start of suspension culture (step (1)), part of the floating cell population-containing medium was transferred using a micropipette to a 15-mL tube, and centrifuged for 5 min at 1000 rpm in a centrifuge (CF8DL; manufactured by Koki Holdings Co., Ltd.). After removal of the supernatant, the STEMdiff+B medium was added to the precipitate. Next, the cells were suspended and seeded at $2 \times 10^5$ cells in 1.5 mL of medium per well of a cell-adherent 6-well plate (manufactured by Corning, Inc.). Then, suspension culture was started (step (3) was started). At Day 14 (Day 4 after the start of step (3)) after the start of suspension culture (step (1)), the resulting cell population was collected by the same procedure as the above collection procedure.

Figure 5:
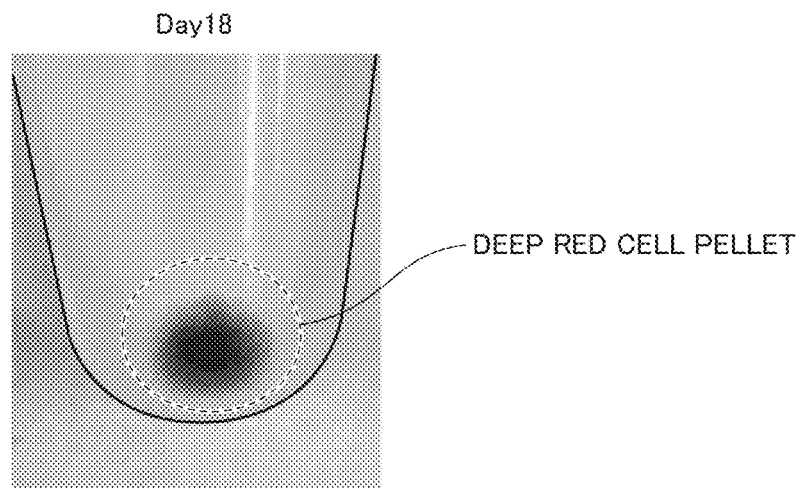
FIG. 5 is a photograph obtained by imaging a cell pellet prepared by collecting and centrifuging an embryonic erythroblast-containing cell population derived from human iPS cells (HC-6 #10 strain) at Day 18 after the start of suspension culture (step (1)) in Example 1.

At Day 14 (Day 4 after the start of step (3)) after the start of suspension culture (step (1)), 1 mL of the STEMdiff+B medium was further added to part of the cells, and the culture continued. At Day 18 (Day 8 after the start of step (3)) after the start of suspension culture (step (1)), the resulting cell population was collected by the same procedure as the above collection procedure. When observed, the resulting cell pellet exhibited a very deep red color (FIG. 5).

<To Evaluate Cell Population by Immunostaining>

The percentage of embryonic erythroblasts among cells included in the above cell population was checked by immunostaining. The cell population obtained at Day 10, 14, or 18 after the start of suspension culture (step (1)) was washed with PBS (manufactured by Thermo Fisher Scientific, Inc.), and then fixed for 15 min with 4% paraformaldehyde (manufactured by Wako Pure Chemical Industries, Ltd.). A Cytospin 4 (manufactured by Thermo Fisher Scientific, Inc.) and Cytofunnels (manufactured by Thermo Fisher Scientific, Inc.) were used to prepare a smear sample on each slide glass. Next, membrane permeabilization was performed for 5 min by using 0.2% Triton X-100 (manufactured by Wako Pure Chemical Industries, Ltd.)-containing TBS (manufactured by TAKARA BIO INC.). Then, the above slide glass was subjected to blocking for 1 to 3 h by using Superblock Blocking Buffer (manufactured by Thermo Fisher Scientific, Inc.). This was followed by fluorescent immunostaining using an antibody (diluted 750-fold; manufactured by Genetex, Inc.) against ε-globin (HBE1), an embryonic erythroblast marker, and an antibody (diluted 100-fold; manufactured by Novusbio, Inc.) against glycophorin A (GPA), an erythroblast marker. As a fluorescently labeled secondary antibody, an Alexa 488-labeled donkey anti-rabbit antibody and a donkey anti-mouse antibody (diluted 1000-fold; manufactured by Thermo Fisher Scientific, Inc.) were used respectively. In addition, 2 μg/ml of Hoechst 33342 (manufactured by DOJINDO LABORATORIES) was added to the diluted secondary antibody solution so as to compare the nuclear staining. An upright fluorescence microscope Axio Imager M2 (manufactured by Carl Zeiss, Inc.) and accessory software Axio Vision were used to observe stained cells and acquire their images.

Figure 6:
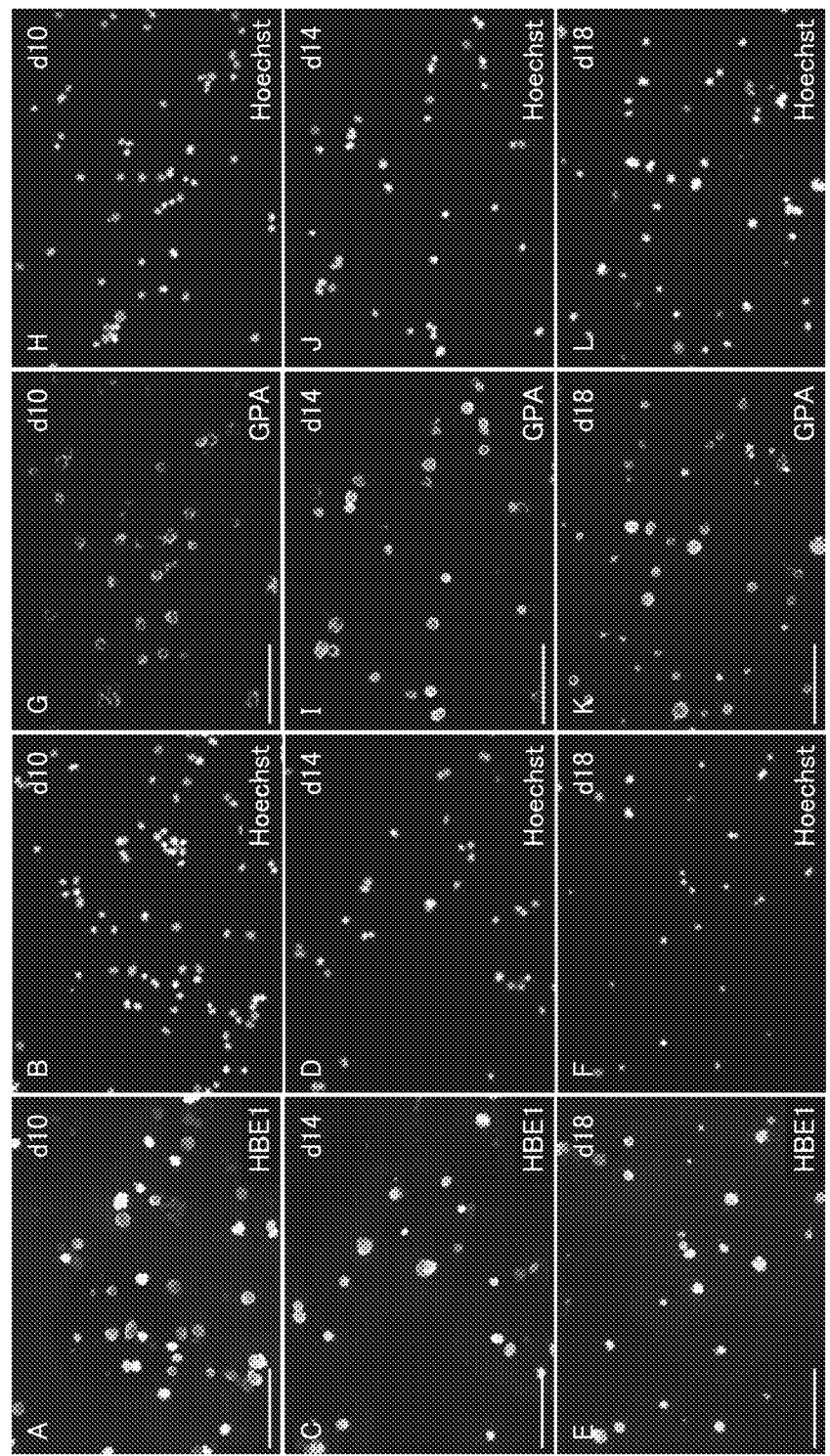
FIG. 6 is fluorescent micrographs obtained by fluorescent immunostaining of an embryonic erythroblast-containing cell population derived from human iPS cells (HC-6 #10 strain) at Day 10, Day 14, or Day 18 after the start of suspension culture (step (1)) in Example 1. A and B, C and D, or E and F represent an ε-globin (HBE1) staining image and its nuclear staining image at Day 10, Day 14, or Day 18, respectively, after the start of suspension culture (step (1)). G and H, I and J, or K and L represent a glycophorin A (GPA) staining image and its nuclear staining image at Day 10, Day 14, or Day 18, respectively, after the start of suspension culture (step (1)). The scale bars in A, C, E, G, I, and K each indicate 100 µm.

FIG. 6 shows the results of staining images. About 80% or more of the cells obtained at Day 10 after the start of suspension culture (step (1)) were found ε-globin positive and glycophorin A positive (FIGS. 6A, B, G, and H). The cell population abundantly containing embryonic erythroblasts was demonstrated to be successfully produced from human iPS cells by the production method of the invention. In addition, about 80% or more of the cell population obtained at Day 14 or 18 after the start of suspension culture (step (1)) was found ε-globin positive and glycophorin A positive (FIGS. 6C, D, I, and J and FIGS. 6E, F, K, and L). It has been demonstrated that the percentage of embryonic erythroblasts in a cell population after the cell population is continuously cultured can be kept high by the production method of the invention.

<To Evaluate Cell Population by Real-Time PCR>

The percentage of expression of the β-globin gene family expressed in cells of the above cell population was checked by real-time PCR. The floating cell population-containing medium at Day 10, 14, or 18 after the start of suspension culture (step (1)) was centrifuged for 5 min at 1000 rpm in a centrifuge (CF8DL; manufactured by Koki Holdings Co., Ltd.) to remove the supernatant. The resulting cells were washed with PBS (manufactured by Thermo Fisher Scientific, Inc.), centrifuged for 3 min at 7500 rpm in a centrifuge (centrifuge 5424; manufactured by Eppendorf, Inc.), and then subjected to total RNA extraction from the cells using an RNeasy Micro Kit (manufactured by QIAGEN, Inc.). The resulting total RNA was subjected to reverse transcription using SuperScript III (manufactured by Thermo Fisher Scientific, Inc.). Subsequently, the resulting cDNA was used as a template to perform real-time PCR by using TaqMan probes (manufactured by Thermo Fisher Scientific, Inc.) and a TaqMan Fast Advanced Master Mix (manufactured by Thermo Fisher Scientific, Inc.) in a 96-well plate under Fast PCR conditions according to the instruction in the package insert. The TaqMan probes used were human probes designated in Table 2.

The gene product containing a TaqMan probe target sequence for each member of the β-globin gene family, namely ε-globin, γ-globin, or β-globin, was used to draw a standard curve. Then, the mRNA copy number for each β-globin gene family member expressed was quantified. The value obtained by dividing the copy number for each β-globin gene family member expressed by the total β-globin gene family copy number was shown as the percentage of expression of each β-globin gene family member. The production of embryonic erythroblast-containing cell population and the analysis by real-time PCR were independently triplicated to calculate the average and the standard error.

Table 3 shows the results. In any of the cell population at Day 10, 14, or 18 after the start of suspension culture (step (1)), about 60% or more of all the β-globin gene family members were ε-globin gene, an embryonic erythroblast marker. According to the production method of the invention, the cell population with increased levels of expression of ε-globin was demonstrated to be successfully produced from human iPS cells. In addition, according to the production method of the invention, it has also been demonstrated that the expression of ε-globin can be kept high even after the cell population is continuously cultured. Besides, even when three independent experiments were conducted, the standard error was sufficiently small. Thus, the production method of the invention can be said to be a highly-reproducible method.

TABLE 2

TaqMan probes used in real-time PCR

| Gene name | Animal species | Product number |
|---|---|---|
| HBE1 | Human | Hs00362216_m1 |
| HBG2/1 | Human | Hs00361131_g1 |
| HBB | Human | Hs00758889_s1 |
| Hbe1 | Rat | Rn01754780_g1 |
| Hbg1 | Rat | Rn00756487_mH |
| Hbb | Rat | Rn00583657_g1 |

TABLE 3

Relative expression levels (%) of the β-globin gene family in human iPS cell-derived erythroblasts

| | Day 10 | Day 14 | Day 18 |
|---|---|---|---|
| ε-Globin (HBE1) | 65 ± 3.6 | 61 ± 4.2 | 65 ± 2.4 |
| γ-Globin (HBG2/1) | 35 ± 3.6 | 39 ± 4.2 | 35 ± 2.4 |
| β-Globin (HBB) | 0 ± 0.0 | 0 ± 0.0 | 0 ± 0.0 |

Example 2: Embryonic Erythroblast-Containing Cell Population Produced from Rat ES Cells <Maintenance Culture>

Rat ES cells (derived from a DA rat; obtained from DS Pharma Biomedical Co., Ltd.) were seeded on mitomycin C-treated mouse fibroblasts (manufactured by ReproCELL Inc.), and were subjected to maintenance culture under conditions at 37° C. and 5% $CO_2$. At that time, the medium used was StemMedium (manufactured by DS Pharma Biomedical Co., Ltd.) containing A-83-01 (at a final concentration of 0.5 μM; manufactured by Wako Pure Chemical Industries, Ltd.), CHIR99021 (at a final concentration of 3 μM; manufactured by Cayman Chemical, Inc.), Y-27632 (at a final concentration of 10 μM), 1% Antibiotic-Antimycotic (manufactured by Thermo Fisher Scientific, Inc.), rat LIF (at a final concentration of 2000 U/mL; manufactured by Millipore, Inc.), and 2-mercaptoethanol (at a final concentration of 0.1 mM; manufactured by Wako Pure Chemical Industries, Ltd.) (hereinafter, referred to as "rat ES medium").

As a specific maintenance culture operation, colonies of rat ES cell line in a floating state were collected into a 15-mL centrifuge tube, and centrifuged for 3 min at 1000 rpm in a centrifuge (CF8DL; manufactured by Koki Holdings Co., Ltd.) to remove the supernatant. Next, Accutase (manufactured by Innovative Cell Technologies, Inc.) was used for enzymatic treatment, followed by pipetting and dispersing the remainder into single cells. Then, the rat ES cells, which had been dispersed into single cells, were centrifuged to remove the supernatant. Subsequently, the rat ES medium was added, and the cells were dispersed into single cells by pipetting. After that, the rat ES cells, which had been dispersed into single cells, were seeded on a plastic culture dish where mitomycin C-treated mouse fibroblasts (manufactured by ReproCELL Inc.) had been seeded, and were subjected to suspension culture under conditions at 37° C. and 5% $CO_2$. In the case of using, as the plastic culture dish, a 10-cm dish (for cell culture; manufactured by Corning, Inc.), the number of seeded rat ES cells, which had been dispersed into single cells, was from $0.9 \times 10^5$ to $1.8 \times 10^5$. This was followed by culturing for 3 to 4 days.

<Step (1)>

Figure 7:
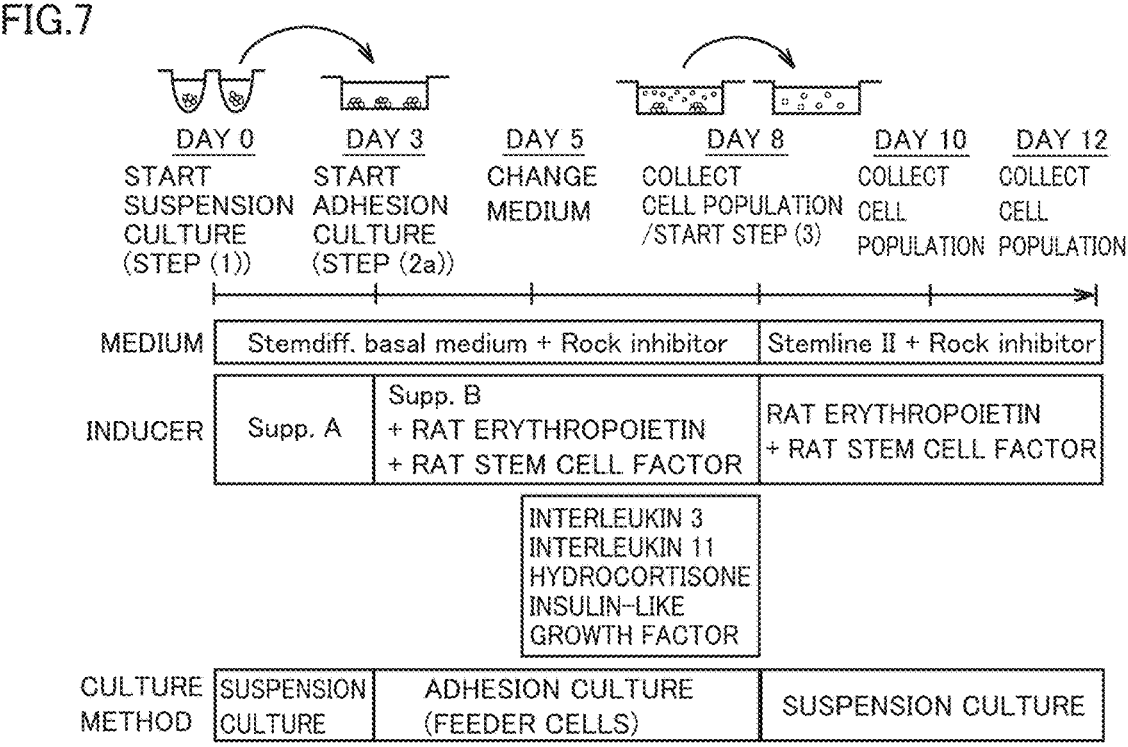
FIG. 7 is a diagram schematically illustrating a procedure when an embryonic erythroblast-containing cell population was produced from rat ES cells in Example 2. The days in the diagram each indicate the number of days from the start of step (1).

According to the procedure illustrated in FIG. 7, differentiation of rat ES cells was started to be induced. Colonies of prepared rat ES cell line in a floating state were collected into a 15-mL centrifuge tube, and centrifuged for 5 min at 1000 rpm in a centrifuge (CF8DL; manufactured by Koki Holdings Co., Ltd.) to remove the supernatant. Next, Accutase (manufactured by Innovative Cell Technologies, Inc.) was used for enzymatic treatment, followed by pipetting and dispersing the remainder into single cells. Then, the rat ES cells, which had been dispersed into single cells, were centrifuged to remove the supernatant. The rat ES cells were suspended in STEMdiff+A medium, and were seeded at $3 \times 10^3$ cells in 75 μL of medium per well of a non-cell-adherent 96-well culture plate (PrimeSurface 96-well V-bottom plate; manufactured by Sumitomo Bakelite Co., Ltd.) in the presence of Y27632 (at a final concentration of 20 μM).

The culture plate was centrifuged for 5 min at 1000 rpm in a centrifuge (CF8DL, manufactured by Koki Holdings Co., Ltd.), and the cells were subjected to suspension culture under conditions at 37° C. and 5% $CO_2$ (step (1) was started).

<Step (2)>

Feeder cells for performing step (2a) were beforehand provided. The feeder cells used were OP9 cells (mouse bone marrow stroma cells; obtained from ATCC). The OP9 cells were subjected to maintenance culture on a 10-cm dish (manufactured by Corning, Inc.) using αMEM medium (manufactured by NACALAI TESQUE, INC.) containing 10% FBS (manufactured by Corning, Inc.) and 1% penicillin-streptomycin (manufactured by Sigma-Aldrich Co. LLC) (hereinafter, referred to as "OP9 medium"). The cells were subcultured once every 3 to 4 days. The subculturing procedure included: removing supernatant from a dish to which OP9 cells are attached; washing the cells with PBS; using 0.25% Trypsin/1 mM EDTA solution (manufactured by NACALAI TESQUE, INC.) to carry out enzymatic treatment; and then adding OP9 medium and pipetting and collecting the OP9 cells. The OP9 cells were centrifuged for 3 min at 1000 rpm in a centrifuge (CF8DL; manufactured by Koki Holdings Co., Ltd.) to remove the supernatant, were suspended in OP9 medium at from $1 \times 10^5$ to $2 \times 10^5$ cells per dish, and then cultured under conditions at 37° C. and 5% $CO_2$. At the time of use as feeder cells, the OP9 cells were suspended at $4.5 \times 10^4$ cells per well in OP9 medium, seeded on a 6-well plate (manufactured by Corning, Inc.) coated with growth factor-reduced Matrigel (manufactured by Corning, Inc.) diluted 20-fold, and cultured under conditions at 37° C. and 5% $CO_2$. At Day 3 of culturing, the cells were treated with mitomycin C (manufactured by NACALAI TESQUE, INC.), and were used as feeder cells.

Figure 8:
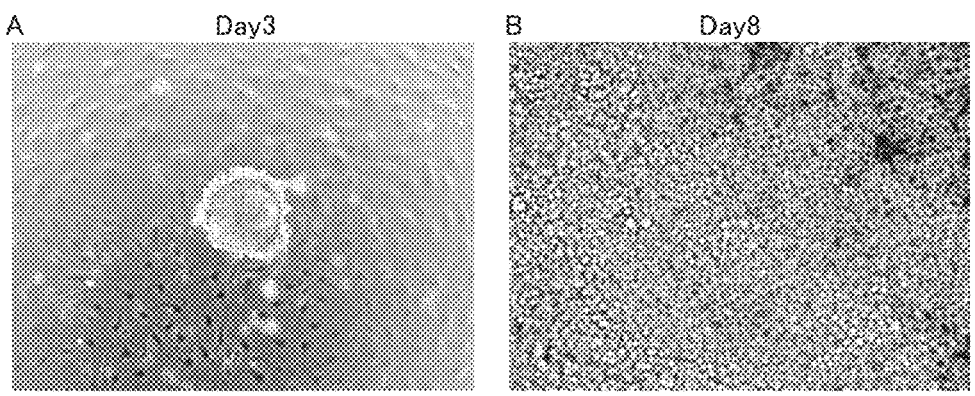
FIG. 8A is a bright-field image, observed under an inverted microscope, of a cell aggregate derived from rat ES cells at Day 3 after the start of suspension culture (step (1)) in Example 2.
FIG. 8B is a bright-field image, observed under an inverted microscope, of a floating embryonic erythroblast-containing cell population at Day 8 after the start of suspension culture (step (1)).

Five pieces of cell aggregate derived from the rat ES cells at Day 3 after the start of suspension culture (step (1)) were transferred, using a micropipette, per well of the above 6-well plate, and were subjected to adhesion culture under conditions at 37° C. and 5% $CO_2$ (step (2a) was started). In addition, the medium used was 1 mL per well of a mixed medium (manufactured by STEMCELL Technologies, Inc.) of STEMdiff Hematopoietic Basal Medium and STEMdiff Hematopoietic Supplement B supplemented with rat recombinant stem cell factor (at a final concentration of 30 ng/mL; manufactured by R&D Systems, Inc.) and Y27632 (at a final concentration of 20 μM) (hereinafter, referred to as "rat STEMdiff+B medium"), the medium further containing rat recombinant erythropoietin (at 30 ng/mL; manufactured by R&D Systems, Inc.). How a cell aggregate looked from the start of suspension culture (step (1)) to Day 3 (immediately after the start of step (2a)) was observed in the bright field with an inverted microscope (BIOREVO; manufactured by KEYENCE CORPORATION) (FIG. 8A).

The medium was removed from the 6-well plate at Day 5 (Day 2 after the start of step (2a)) after the start of suspension culture (step (1)), and 1 mL of medium was added, the medium being rat STEMdiff+B medium containing hydrocortisone (at a final concentration of 1 μM; manufactured by Wako Pure Chemical Industries, Ltd.), rat recombinant interleukin 3 (at a final concentration of 10 ng/mL; manufactured by R&D Systems, Inc.), human recombinant interleukin 11 (at a final concentration of 20 ng/mL; manufactured by R&D Systems, Inc.), human recombinant insulin-like growth factor 1 (at a final concentration of 20 ng/mL; manufactured by R&D Systems, Inc.), and rat recombinant erythropoietin (at a final concentration of 60 ng/mL; manufactured by R&D Systems, Inc.). A floating cell population in the medium appeared and was observed (FIG. 8B) in the bright field with an inverted microscope at Day 8 (Day 5 after the start of step (2a)) after the start of suspension culture (step (1)).

At Day 8 (Day 5 after the start of step (2a)) after the start of suspension culture (step (1)), the floating cell population, together with the medium, was collected (step (2b)), and then centrifuged for 3 min at 7500 rpm in a centrifuge (centrifuge 5424; manufactured by Eppendorf, Inc.) to remove the supernatant.

<Step (3)>

At Day 8 (Day 5 after the start of step (2a)) after the start of suspension culture (step (1)), part of the floating cell population-containing medium was transferred using a micropipette to a 15-ml tube, and centrifuged for 5 min at 1000 rpm in a centrifuge (CF8DL; manufactured by Koki Holdings Co., Ltd.). After removal of the supernatant, Stemline II medium (manufactured by Sigma-Aldrich Co. LLC) containing rat recombinant erythropoietin (at a final concentration of 60 ng/mL; manufactured by R&D Systems, Inc.), rat recombinant stem cell factor (at a final concentration of 30 ng/mL; manufactured by R&D Systems, inc.), and Y27632 (at a final concentration of 20 μM; manufactured by Wako Pure Chemical Industries, Ltd.) (hereinafter, referred to as rat Stemline II medium) was added to the resulting precipitate. The cells were then suspended therein, and suspension culture was started on a cell-adherent 6-well plate (manufactured by Corning, Inc.) (step (3) was started). The cells were seeded at $2 \times 10^5$ cells per well in 1.5 ml of rat Stemline II medium. At Day 10 (Day 2 after the start of step (3)) after the start of suspension culture (step (1)), the resulting cell population was collected by the same procedure as the above collection procedure.

Figure 9:
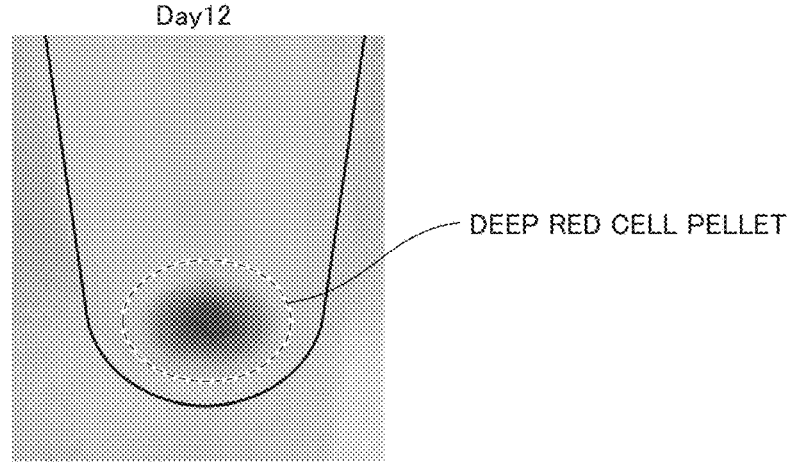
FIG. 9 is a photograph obtained by imaging a pellet prepared by collecting and centrifuging an embryonic erythroblast-containing cell population derived from rat ES cells at Day 12 after the start of suspension culture (step (1)) in Example 2.

At Day 10 (Day 2 after the start of step (3)) after the start of suspension culture (step (1)), 1 mL of rat Stemline II medium was added to part of the cells, and the culture continued. At Day 12 (Day 4 after the start of step (3)) after the start of suspension culture (step (1)), the resulting cell population was collected by the same procedure as the above collection procedure. When observed, the resulting cell pellet exhibited a very deep red color (FIG. 9).

<To Evaluate Cell Population by Immunostaining>

The cell population obtained at Day 8, 10, or 12 after the start of suspension culture (step (1)) was subjected to immunostaining to check the percentage of embryonic erythroblasts. The immunostaining was performed by the same protocol as in Example 1. The primary antibody used was an antibody (diluted 750-fold; manufactured by Genetex, Inc.) against ε-globin (HBE1), an embryonic erythroblast marker. As a fluorescently labeled secondary antibody, an Alexa 488-labeled donkey anti-rabbit antibody (diluted 1000-fold; manufactured by Thermo Fisher Scientific, Inc.) was used. An upright fluorescence microscope Axio Imager M2 (manufactured by Carl Zeiss, Inc.) and accessory software Axio Vision were used to observe stained cells and acquire their images.

Figure 10:
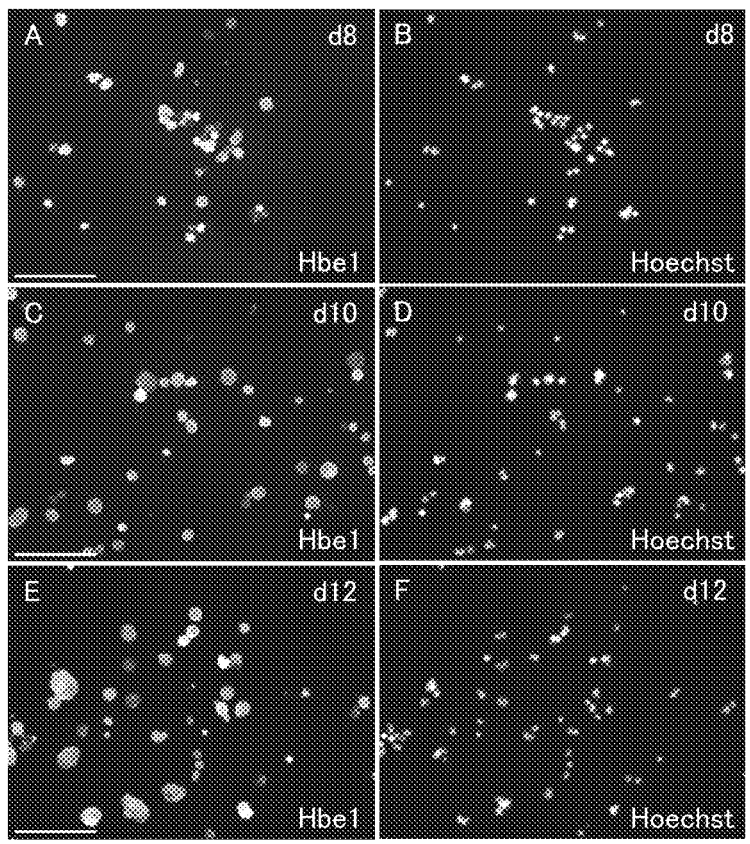
FIG. 10 is fluorescent micrographs obtained by fluorescent immunostaining of an embryonic erythroblast-containing cell population derived from rat ES cells at Day 8, Day 10, or Day 12 after the start of suspension culture (step (1)) in Example 2. A and B, C and D, or E and F represent an Hbe1 staining image and its nuclear staining image at Day 8, Day 10, or Day 12, respectively, after the start of suspension culture (step (1)). The scale bars in A, C, and E each indicate 100 μm.

FIG. 10 shows the staining results. About 80% or more of the cells obtained at Day 8 after the start of suspension culture (step (1)) were found ε-globin positive (FIGS. 10A and B). The cell population abundantly containing embryonic erythroblasts was demonstrated to be successfully produced from rat ES cells by the production method of the invention. In addition, about 80% or more of cells in the cell population obtained at Day 10 or 12 after the start of suspension culture (step (1)) were also found ε-globin positive (FIGS. 10C to F). According to the production method of the invention, it has also been demonstrated that the percentage of embryonic erythroblasts can be kept high even after the cell population is continuously cultured.

<To Evaluate Cell Population by Real-Time PCR>

The percentage of expression of the β-globin gene family expressed in cells of the above cell population at Day 10 or 12 after the start of the above suspension culture (step (1)) was calculated. The real-time PCR was performed by the same protocol as in Example 1. The TaqMan probes used were rat probes designated in Table 2.

The gene product containing a TaqMan probe target sequence for each member of the β-globin gene family, namely ε-globin, γ-globin, or β-globin, was used to draw a standard curve. Then, the mRNA copy number for each β-globin gene family member expressed was quantified. The value obtained by dividing the copy number for each β-globin gene family member by the total β-globin gene family copy number was shown as the percentage of expression of each β-globin gene family member. The production of embryonic erythroblast-containing cell population and the analysis by real-time PCR were independently triplicated to calculate the average and the standard error.

Table 4 shows the results. In any of the cell population at Day 10 or 12 after the start of suspension culture (step (1)), about 60% or more of all the β-globin gene family were ε-globin gene, an embryonic erythroblast marker. According to the production method of the invention, the cell population with increased levels of expression of ε-globin was demonstrated to be successfully produced from rat ES cells. In addition, according to the production method of the invention, it has also been demonstrated that a cell population, in which expression of ε-globin can be kept high even after the cell population is continuously cultured, can be obtained. Besides, even when three independent experiments were conducted, the standard error was sufficiently small. Thus, the production method of the invention can be said to be a highly-reproducible method.

TABLE 4

Relative expression levels (%) of the β-globin gene family in rat ES cell-derived erythroblasts

| | Day 10 | Day 12 |
|---|---|---|
| ε-Globin (Hbe1) | 62 ± 1.6 | 62 ± 3.4 |
| γ-Globin (Hbg1) | 36 ± 1.4 | 22 ± 1.0 |
| β-Globin (Hbb) | 2 ± 0.5 | 16 ± 2.4 |

Reference Example 1: To Evaluate Culture and Differentiation Stage of K562 Cells Human chronic myeloid leukemia-derived cell line K562 cells (obtained from Health Science Research Resources Bank) were used as other hematopoietic cells to check expression of ε-globin. K562 cells were cultured and maintained as follows. RPMI medium (Roswell Park Memorial Institute 1640; manufactured by Thermo Fisher Scientific, Inc.) containing 10% FBS (manufactured by Corning, Inc.) and 1% penicillin-streptomycin (manufactured by Sigma-Aldrich Co. LLC) (hereinafter, referred to as "K562 medium") was used, and the cells were subjected to suspension culture on a low-adherent 6-cm dish (manufactured by Sumitomo Bakelite Co., Ltd.). The floating cell-containing medium was collected once every 7 days, and centrifuged for 5 min at 1000 rpm in a centrifuge (SCTSBA; manufactured by Koki Holdings Co., Ltd.) to remove the supernatant. The K562 cells were suspended in 5 mL of K562 medium and seeded at $5\times10^5$ cells per dish, and cultured under conditions at 37° C. and 5% $CO_2$.

It has been known that addition of an inducer (sodium butyrate) causes an increase in the expression of εs-globin in K562 cells. Thus, a change in expression of ε-globin after addition of sodium butyrate was checked over time. For differentiation culture of K562 cells, K562 medium containing 1 mM sodium butyrate (manufactured by Sigma-Aldrich Co. LLC) was used. The cells were suspended in 5 mL of the above medium and seeded at $5\times10^5$ cells per low-adherent 6-cm dish, and cultured under conditions at 37° C. and 5% $CO_2$. The floating cell-containing medium was collected at Day 0, 2, 4, or 8 after the start of differentiation culture, and centrifuged for 5 min at 1000 rpm in a centrifuge (SCTSBA; manufactured by Koki Holdings Co., Ltd.) to remove the supernatant.

Like the evaluation protocol by real-time PCR in Example 1, the percentage of expression of each β-globin gene family member expressed in cells was determined by real-time PCR. Table 5 shows the results. About 30% or less of the β-globin gene family were an embryonic erythroblast marker ε-globin gene under any of the conditions.

TABLE 5

Relative expression levels (%) of the β-globin gene family in K562 cells

| | Day 0 | Day 2 | Day 4 | Day 8 |
|---|---|---|---|---|
| ε-Globin (HBE1) | 4 ± 0.5 | 25 ± 1.6 | 27 ± 1.3 | 30 ± 1.9 |
| γ-Globin (HBG2/1) | 96 ± 0.5 | 75 ± 1.6 | 73 ± 1.3 | 70 ± 1.9 |
| β-Globin (HBB) | 0 ± 0.0 | 0 ± 0.0 | 0 ± 0.0 | 0 ± 0.0 |

Reference Example 2: To Evaluate Culture and Differentiation Stage of REL Cells

REL cells, rat erythroleukemia cells, (obtained from Institute of Molecular Genetics and Genetic Engineering (Prof. Popovic Serbia)) were used as other hematopoietic cells to check a change in expression of ε-globin gene. REL cells were cultured and maintained as follows. RPMI medium (Roswell Park Memorial Institute 1640; manufactured by Thermo Fisher Scientific, Inc.) containing 40% FBS (manufactured by Corning, Inc.) and 1% penicillin-streptomycin (manufactured by Sigma-Aldrich Co. LLC) (hereinafter, referred to as "REL medium") was used, and the cells were subjected to suspension culture on a low-adherent 6-cm dish (manufactured by Sumitomo Bakelite Co., Ltd.). The floating cell-containing medium was collected once every 2 days, and centrifuged for 5 min at 1000 rpm in a centrifuge (SCT5BA; manufactured by Koki Holdings Co., Ltd.) to remove the supernatant. The REL cells were suspended in 5 mL of REL medium and seeded at $5\times10^5$ cells per dish, and cultured under conditions at 37° C. and 5% $CO_2$.

An inducer (hexamethylene bisacetamide: HMBA) was added to REL cells to check a change in expression of ε-globin over time. For differentiation culture of REL cells, the medium used was REL medium containing HMBA (at a final concentration of 1 mM; manufactured by Sigma-Aldrich Co. LLC.). The REL cells were suspended in 5 mL of the above medium and seeded at $5\times10^5$ cells per low-adherent 6-cm dish (manufactured by Sumitomo Bakelite Co., Ltd.), and then cultured under conditions at 37° C. and 5% $CO_2$. The floating cell-containing medium was collected at Day 0, 2, 4, or 8 after the start of differentiation culture, and centrifuged for 5 min at 1000 rpm in a centrifuge (SCT5BA; manufactured by Koki Holdings Co., Ltd.) to remove the supernatant.

Like the evaluation protocol by real-time PCR in Example 1, the percentage of expression of each β-globin gene family member expressed in cells was determined by real-time PCR. Table 6 shows the results. Almost all of the β-globin gene family were an adult erythroblast marker β-globin gene under any of the conditions.

TABLE 6

Relative expression levels (%) of the β-globin gene family in REL cells

| | Day 0 | Day 2 | Day 4 | Day 8 |
|---|---|---|---|---|
| ε-Globin (Hbe1) | 0.5 ± 0.1 | 0 ± 0.0 | 0 ± 0.0 | 0 ± 0.0 |
| γ-Globin (Hbg1) | 1.9 ± 0.2 | 0 ± 0.0 | 0 ± 0.0 | 1 ± 0.1 |
| β-Globin (Hbb) | 97.6 ± 0.2 | 100 ± 0.0 | 100 ± 0.0 | 99 ± 0.2 |

Figure 11:
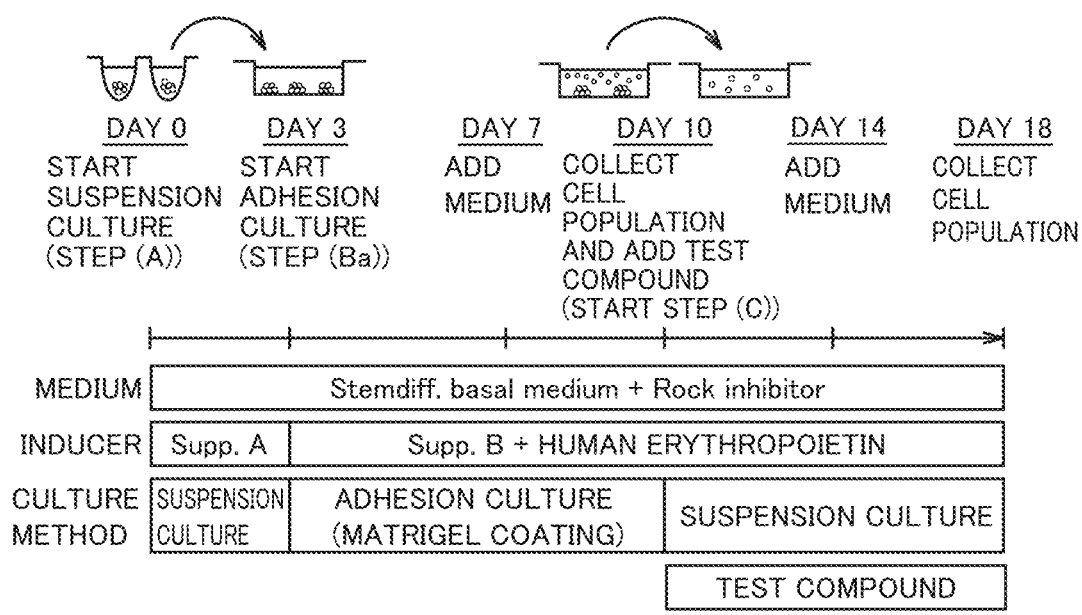
FIG. 11 is a diagram schematically illustrating a procedure of a compound test using an embryonic erythroblast-containing cell population produced from human iPS cells in Example 3. The days in the diagram each indicate the number of days from the start of step (A).

Example 3: Compound Test Using Embryonic Erythroblast-Containing Cell Population Produced from Human iPS Cells The procedure illustrated in FIG. 11 was used to conduct a compound test using an embryonic erythroblast-containing cell population produced from human iPS cells. Differentiation of human iPS cells was induced by substantially the same procedure as in Example 1 to produce an embryonic erythroblast-containing cell population at Day 10 after the start of suspension culture (step (A)) (Step (A) and Step (B)). The cells were centrifuged for 5 min at 1000 rpm in a centrifuge (CF8DL; manufactured by Koki Holdings Co., Ltd.) to remove the supernatant. Next, STEMdiff+B medium was added to the precipitate. Subsequently, the cells were suspended and seeded at $2 \times 10^5$ cells in 1.5 mL of medium per well of a cell-adherent 6-well plate (manufactured by Corning, Inc.). Then, suspension culture was started (step (C) was started). To the medium at that time was added, as a test compound, dihydroartemisinin (hereinafter, referred to as "DHA") (at a final concentration of 0.5 μM or 1 μM) or succinylacetone (hereinafter, referred to as "SA") (at a final concentration of 10 μM or 30 μM). As a solvent control, DMSO was added.

At Day 18 (Day 8 after the start of step (C)) after the start of suspension culture (step (A)), the resulting cell population-containing medium was collected from the 6-well plate. Next, $0.4 \times 10^5$ cells to $1 \times 10^5$ cells were pipetted into an Eppendorf tube, and centrifuged for 3 min at 7500 rpm in a centrifuge (centrifuge 5424; manufactured by Eppendorf, Inc.) to remove the supernatant and give a cell pellet. The concentration of heme or protoporphyrin IX (hereinafter, referred to as "PPIX") included in this cell pellet was quantified using liquid chromatography-mass spectrometry (LC-MS) (step (D)). A change in the concentration of heme or PPIX by addition of a test compound was examined to be able to evaluate how the test compound affected the heme biosynthesis pathway. In addition, the number of cells collected after the culture was counted to determine viability.

Figure 12:
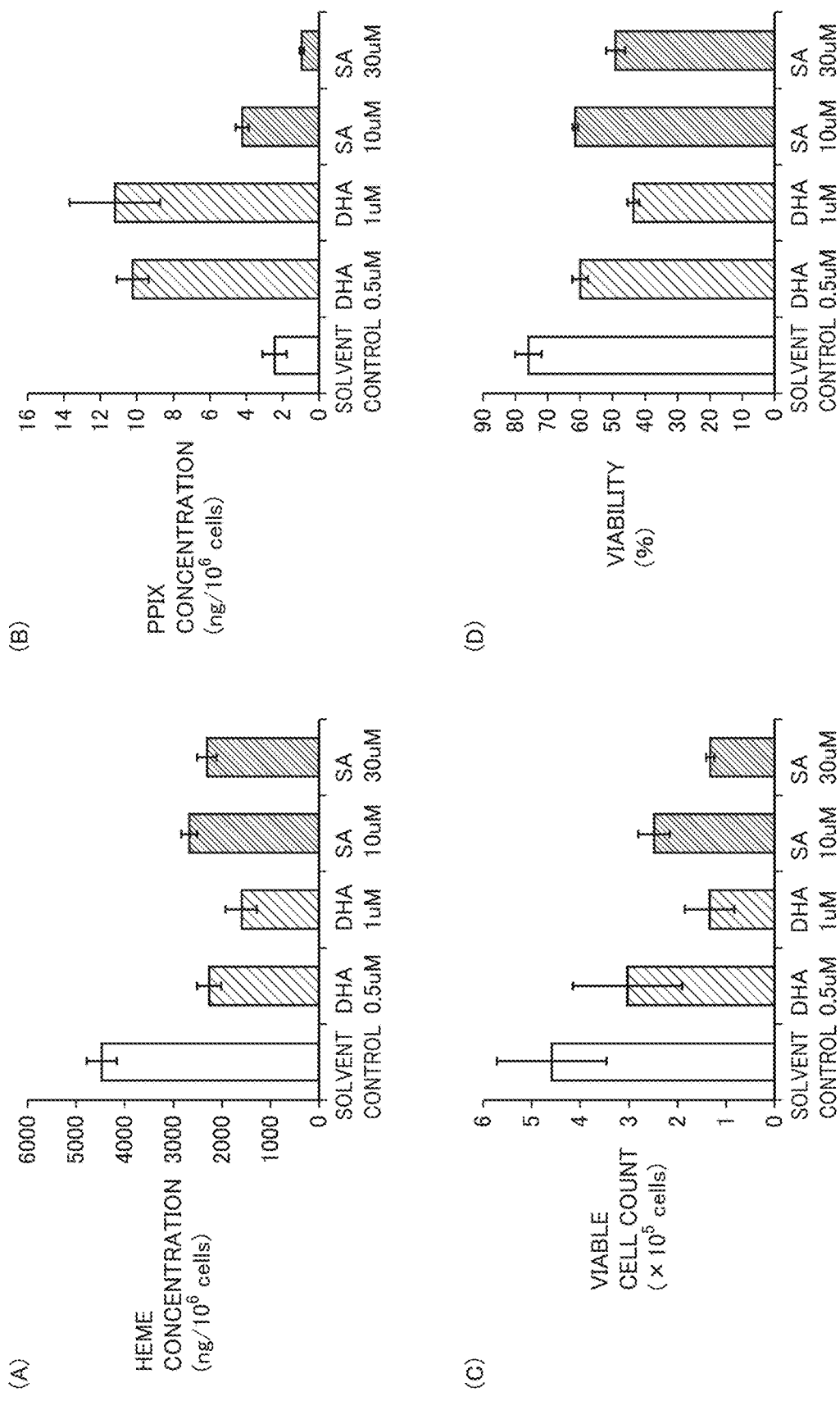
FIG. 12 is graphs for evaluating the effects of test compounds on an embryonic erythroblast-containing cell population in Example 3.

FIG. 12 shows the measured results. The concentration of heme or PPIX was represented in weight per $10^6$ cells (ng/$10^6$ cells). DHA or SA, which is known to inhibit heme synthesis, caused a decrease in the heme concentration at Day 18 (Day 8 after the start of step (C)) after the start of suspension culture (step (A)) when compared to a solvent control (FIG. 12A). While DHA increased the PPIX concentration, SA did not largely affect the PPIX concentration (FIG. 12B). This has suggested that DHA can accumulate PPIX by inhibiting a downstream enzyme in the heme biosynthesis pathway whereas SA failed to increase the PPIX concentration because an upstream enzyme in the heme biosynthesis pathway is blocked. A hypothesis that DHA can induce anemia by inhibiting the most downstream ferrochelatase has been proposed (Clark et al. (2018) Birth Defects Research 110: 553-578). SA reportedly inhibits aminolevulinic acid dehydrogenase acting upstream in the biosynthesis pathway (Sassa et al. (1983). The Journal of Clinical Investigation 71: 625-634). In addition, DHA or SA decreased the viable cell count and viability of cells included in the cell population (FIGS. 12C and D). In Example 1, the cell population included embryonic erythroblasts at a high percentage. Thus, the compound test method of the invention has been demonstrated to be able to evaluate, with precision, the effects of a test compound on embryonic erythroblasts.

Figure 13:
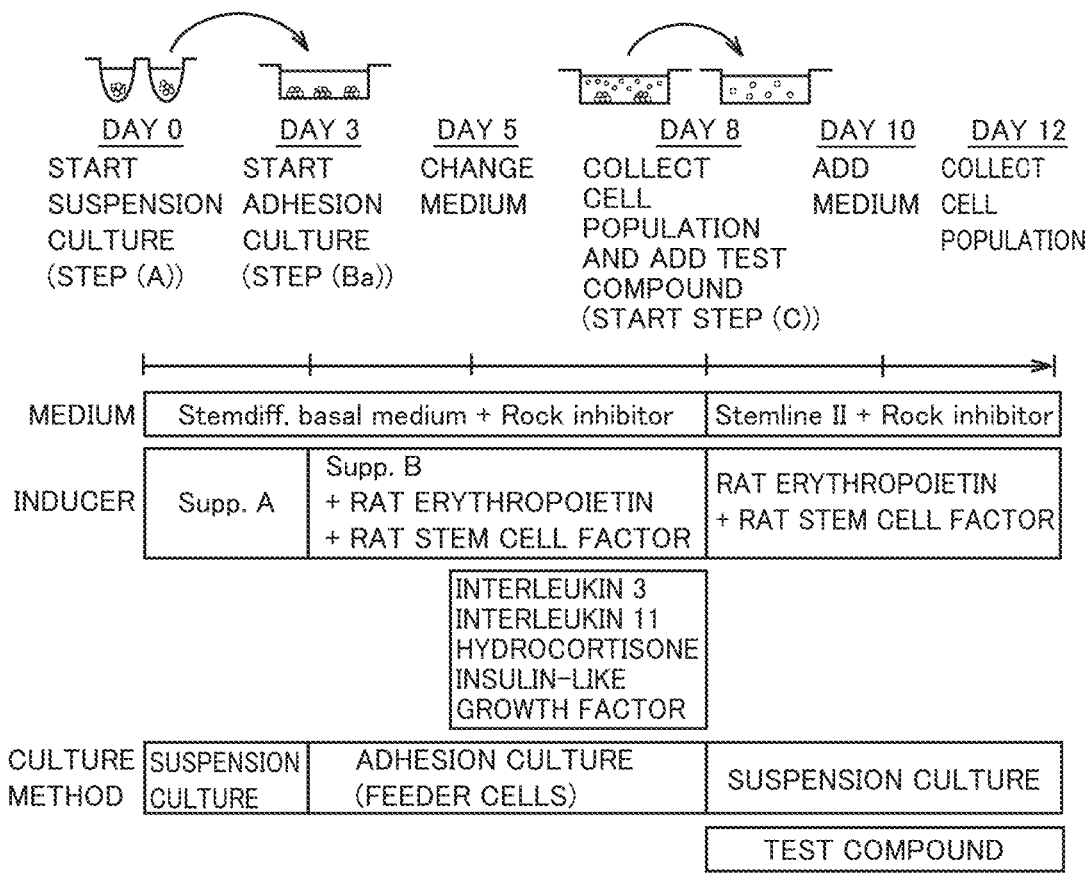
FIG. 13 is a diagram schematically illustrating a procedure of a compound test using an embryonic erythroblast-containing cell population produced from rat ES cells in Example 4. The days in the diagram each indicate the number of days from the start of step (A).

Example 4: Compound Test Using Embryonic Erythroblast-Containing Cell Population Produced from Rat ES Cells The procedure illustrated in FIG. 13 was used to conduct a compound test using an embryonic erythroblast-containing cell population produced from rat ES cells. Differentiation of rat ES cells was induced by substantially the same procedure as in Example 2 to produce an embryonic erythroblast-containing cell population at Day 8 after the start of suspension culture (step (A)) (Step (A) and Step (B)). The cells were centrifuged for 5 min at 1000 rpm in a centrifuge (CF8DL; manufactured by Koki Holdings Co., Ltd.) to remove the supernatant. Next, rat Stemline II medium was added to the precipitate. Subsequently, the cells were suspended and seeded at $2 \times 10^5$ cells in 1.5 mL of medium per well of a cell-adherent 6-well plate (manufactured by Corning, Inc.). Then, suspension culture was started (step (C) was started). To the medium at that time was added, as a test compound, DHA (at a final concentration of 0.5 μM). As a solvent control, DMSO was added.

At Day 12 (Day 4 after the start of step (C)) after the start of suspension culture (step (A)), the resulting cell population-containing medium was collected from the 6-well plate. Next, $0.35 \times 10^5$ cells to $1 \times 10^5$ cells were pipetted into an Eppendorf tube, and centrifuged for 3 min at 7500 rpm in a centrifuge (centrifuge 5424; manufactured by Eppendorf, Inc.) to remove the supernatant and give a cell precipitate. The concentration of heme included in this cell precipitate was quantified using liquid chromatography-mass spectrometry (LC-MS) (step (D)). A change in the heme concentration by addition of the test compound was examined to be able to evaluate how the test compound affected the heme synthesis.

Figure 14:
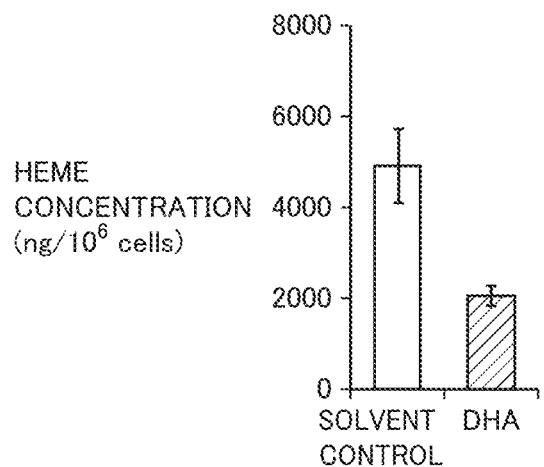
FIG. 14 is a graph for evaluating the effects of a test compound on an embryonic erythroblast-containing cell population in Example 4.

FIG. 14 shows the results of measuring the heme concentration. The heme concentration was represented in weight per $10^6$ cells (ng/$10^6$ cells). DHA, which is known to inhibit heme synthesis, caused a decrease in the heme concentration at Day 12 (Day 4 after the start of step (C)) after the start of suspension culture (step (A)) when compared to a solvent control. In Example 2, the cell population included embryonic erythroblasts at a high percentage. Thus, the compound test method of the invention has been demonstrated to be able to evaluate, with precision, the effects of a test compound on embryonic erythroblasts. In addition, the compound test method of the invention has been demonstrated to be able to evaluate the effects of a test compound on a cell population containing embryonic erythroblasts derived from each cell species.

In addition, human pluripotent stem cell-derived embryonic erythroblasts and rat pluripotent stem cell-derived embryonic erythroblasts were compared. The results of Examples 3 and 4 have revealed that the effects of DHA on the heme synthesis inhibition are almost comparable between humans and rats.

Example 5: Embryonic Erythroblast-Containing Cell Population Produced from Human iPS Cells A human iPS cell line other than in Example 1 was used to produce an embryonic erythroblast-containing cell population.

<Maintenance Culture>

Human iPS cells (201B7 strain) were obtained from Kyoto University. The human iPS cells (201B7 strain) were subjected to maintenance culture using the same procedure as the procedure for maintenance culture of human iPS cells described in Example 1.

<Step (1) to Step (3)>

Figure 15:
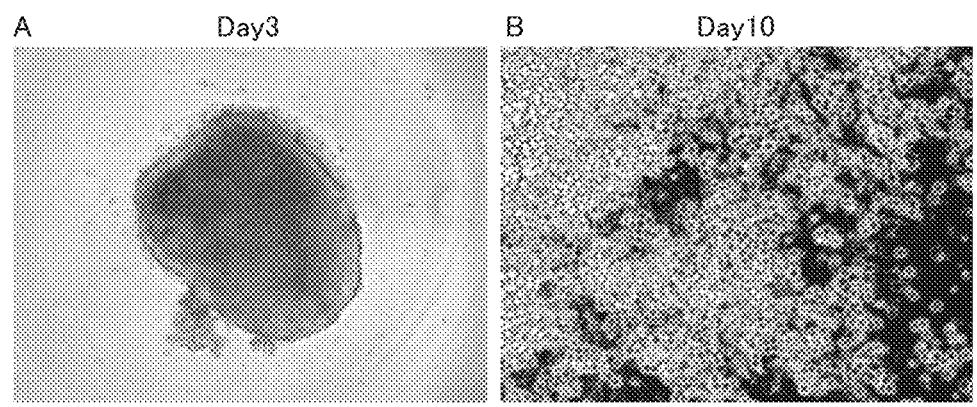
FIG. 15A is a bright-field image, observed under an inverted microscope, of a cell aggregate derived from human iPS cells (201B7 strain) at Day 3 after the start of suspension culture (step (1)) in Example 5.
FIG. 15B is a bright-field image, observed under an inverted microscope, of a floating embryonic erythroblast-containing cell population derived from human iPS cells (201B7 strain) at Day 10 after the start of suspension culture (step (1)).

Differentiation of human iPS cells (201B7 strain) was induced by the same procedure as in Example 1. FIG. 15A shows a bright-field image of a cell aggregate observed at Day 3 (immediately after the start of step (2a)) after the start of suspension culture (step (1)). A floating cell population in the medium was observed (FIG. 15B) at Day 10 (Day 7 after the start of step (2a)) after the start of suspension culture (step (1)).

Figure 16:
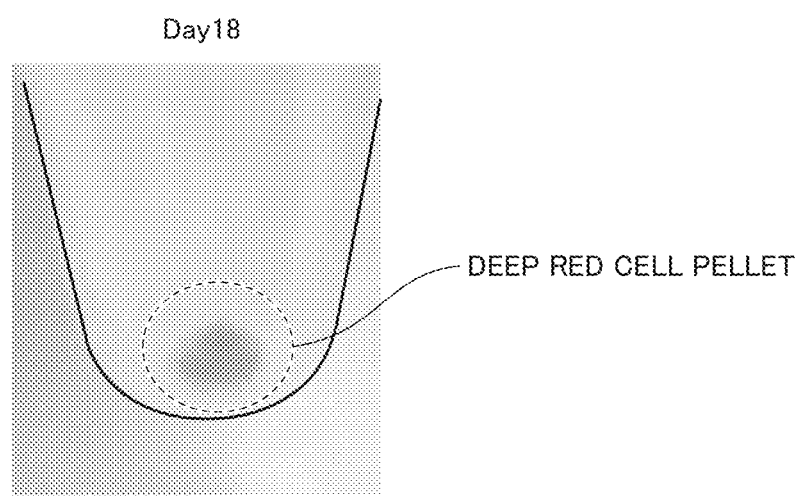
FIG. 16 is a photograph obtained by imaging a cell pellet prepared by collecting and centrifuging an embryonic erythroblast-containing cell population derived from human iPS cells (201B7 strain) at Day 18 after the start of suspension culture (step (1)) in Example 5.

The floating cell population-containing medium was collected at Day 10 (Day 7 after the start of step (2a)) after the start of suspension culture (step (1)), Day 14 (Day 4 after the start of step (3)) after the start of suspension culture (step (1)), or Day 18 (Day 8 after the start of step (3)) after the start of suspension culture (step (1)). The supernatant was then removed to collect a cell population. When observed at Day 18 after the start of suspension culture (step (1)), the resulting cell pellet exhibited a very deep red color (FIG. 16).

<To Evaluate Cell Population by Immunostaining>

The cell population obtained at Day 10, 14, or 18 after the start of suspension culture (step (1)) was subjected to immunostaining to check the percentage of embryonic erythroblasts. The immunostaining was performed by the same protocol as in Example 1.

Figure 17:
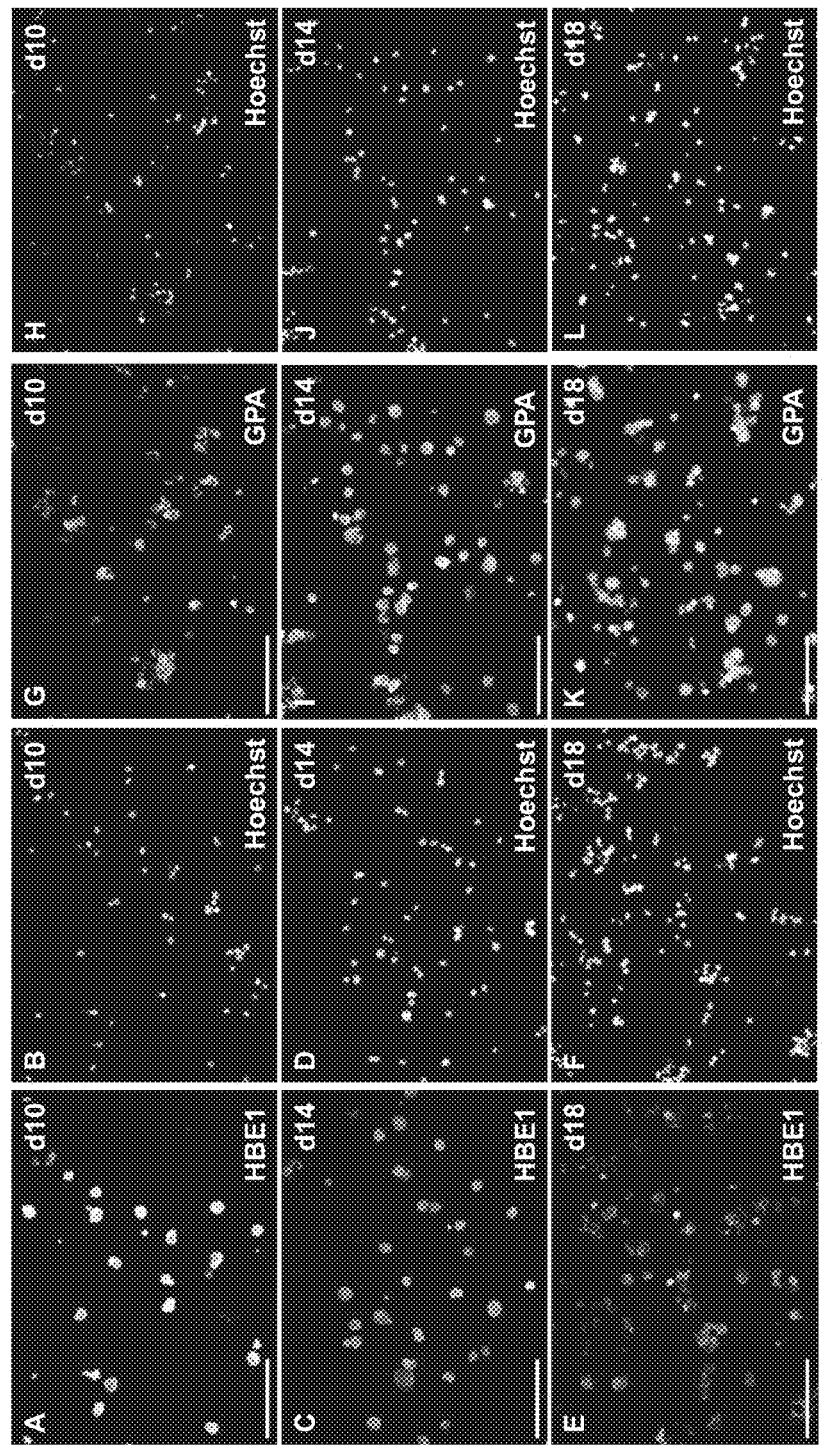
FIG. 17 is fluorescent micrographs obtained by fluorescent immunostaining of an embryonic erythroblast-containing cell population derived from human iPS cells (201B7 strain) at Day 10, Day 14, or Day 18 after the start of suspension culture (step (1)) in Example 5. A and B, C and D, or E and F represent an ε-globin (HBE1) staining image and its nuclear staining image at Day 10, Day 14, or Day 18, respectively, after the start of suspension culture (step (1)). G and H, I and J, or K and L represent a glycophorin A (GPA) staining image and its nuclear staining image at Day 10, Day 14, or Day 18, respectively, after the start of suspension culture (step (1)). The scale bars in A, C, E, G, I, and K each indicate 100 μm.

FIG. 17 shows the results of staining images. About 80% or more of the cells obtained at Day 10 after the start of suspension culture (step (1)) were found ε-globin positive and glycophorin A positive (FIGS. 17A, B, G, and H). The cell population abundantly containing embryonic erythroblasts was demonstrated to be successfully produced from various human iPS cell lines by the production method of the invention. In addition, about 80% or more of the cell population obtained at Day 14 or 18 after the start of suspension culture (step (1)) was found ε-globin positive and glycophorin A positive (FIGS. 17C, D, I, and J and FIGS. 17E, F, K, and L). It has been demonstrated that the percentage of embryonic erythroblasts in a cell population after the cell population is continuously cultured can be kept high by the production method of the invention.

<To Evaluate Cell Population by Real-Time PCR>

The percentage of expression of the β-globin gene family expressed in cells of the above cell population at Day 10, 14, or 18 after the start of suspension culture (step (1)) was checked by real-time PCR. The real-time PCR was performed by the same protocol as in Example 1. The TaqMan probes used were human probes designated in Table 2.

The gene product containing a TaqMan probe target sequence for each member of the β-globin gene family, namely ε-globin, γ-globin, or β-globin, was used to draw a standard curve. Then, the mRNA copy number for each β-globin gene family member expressed was quantified. The value obtained by dividing the copy number for each β-globin gene family member by the total β-globin gene family copy number was shown as the percentage of expression of each β-globin gene family member.

Table 7 shows the results. In any of the cell population at Day 10, 14, or 18 after the start of suspension culture (step (1)), about 60% or more of all the β-globin gene family were ε-globin gene, an embryonic erythroblast marker. According to the production method of the invention, the cell population with increased levels of expression of ε-globin was demonstrated to be successfully produced from various human iPS cell lines. In addition, according to the production method of the invention, it has also been demonstrated that the expression of ε-globin can be kept high even after the cell population is continuously cultured.

TABLE 7

Relative expression levels (%) of the β-globin gene family in human iPS cells (201B7 strain)

|  | Day 10 | Day 14 | Day 18 |
| --- | --- | --- | --- |
| ε-Globin (HBE1) | 65 | 66 | 68 |
| γ-Globin (HBG2/1) | 35 | 34 | 32 |
| β-Globin (HBB) | 0 | 0 | 0 |

Example 6: Embryonic Erythroblast-Containing Cell Population Produced from Human ES Cells <Maintenance Culture>

Human ES cells (KhES-1 strain) were obtained from Kyoto University. The human ES cells were subjected to maintenance culture using the same procedure as the procedure for maintenance culture of human iPS cells described in Example 1.

<Step (1) to Step (3)>

Figure 18:
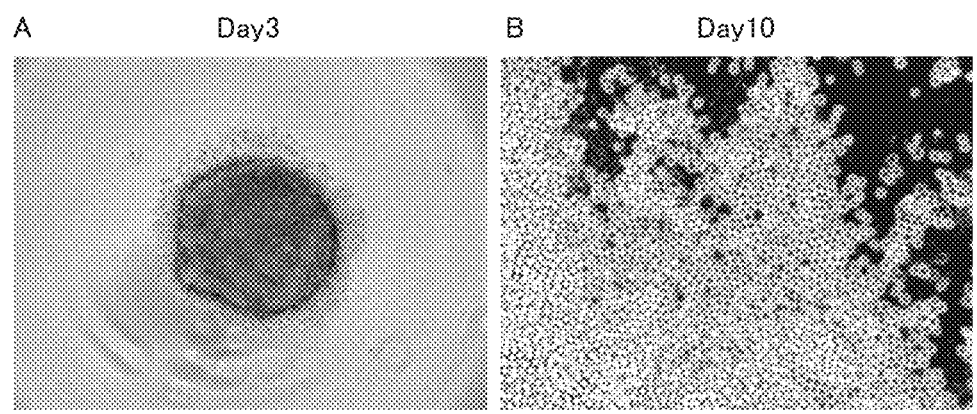
FIG. 18A is a bright-field image, observed under an inverted microscope, of a cell aggregate derived from human ES cells (KhES-1 strain) at Day 3 after the start of suspension culture (step (1)) in Example 6.
FIG. 18B is a bright-field image, observed under an inverted microscope, of a floating embryonic erythroblast-containing cell population derived from human ES cells (KhES-1 strain) at Day 10 after the start of suspension culture (step (1)).

Differentiation of human ES cells was induced by the same procedure as in Example 1. FIG. 18A shows a bright-field image of a cell aggregate observed at Day 3 (immediately after the start of step (2a)) after the start of suspension culture (step (1)). A floating cell population in the medium was observed (FIG. 18B) at Day 10 (Day 7 after the start of step (2a)) after the start of suspension culture (step (1)).

Figure 19:
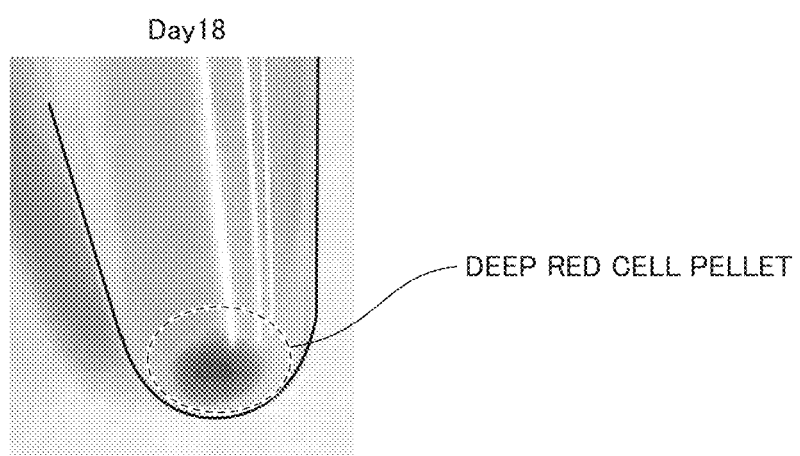
FIG. 19 is a photograph obtained by imaging a cell pellet prepared by collecting and centrifuging an embryonic erythroblast-containing cell population derived from human ES cells (KhES-1 strain) at Day 18 after the start of suspension culture (step (1)) in Example 6.

The floating cell population-containing medium was collected at Day 10 (Day 7 after the start of step (2a)) after the start of suspension culture (step (1)), Day 14 (Day 4 after the start of step (3)) after the start of suspension culture (step (1)), or Day 18 (Day 8 after the start of step (3)) after the start of suspension culture (step (1)). The supernatant was then removed to collect a cell population. When observed at Day 18 after the start of suspension culture (step (1)), the resulting cell pellet exhibited a very deep red color (FIG. 19).

<To Evaluate Cell Population by Immunostaining>

The cell population obtained at Day 10, 14, or 18 after the start of suspension culture (step (1)) was subjected to immunostaining to check the percentage of embryonic erythroblasts. The immunostaining was performed by the same protocol as in Example 1.

Figure 20:
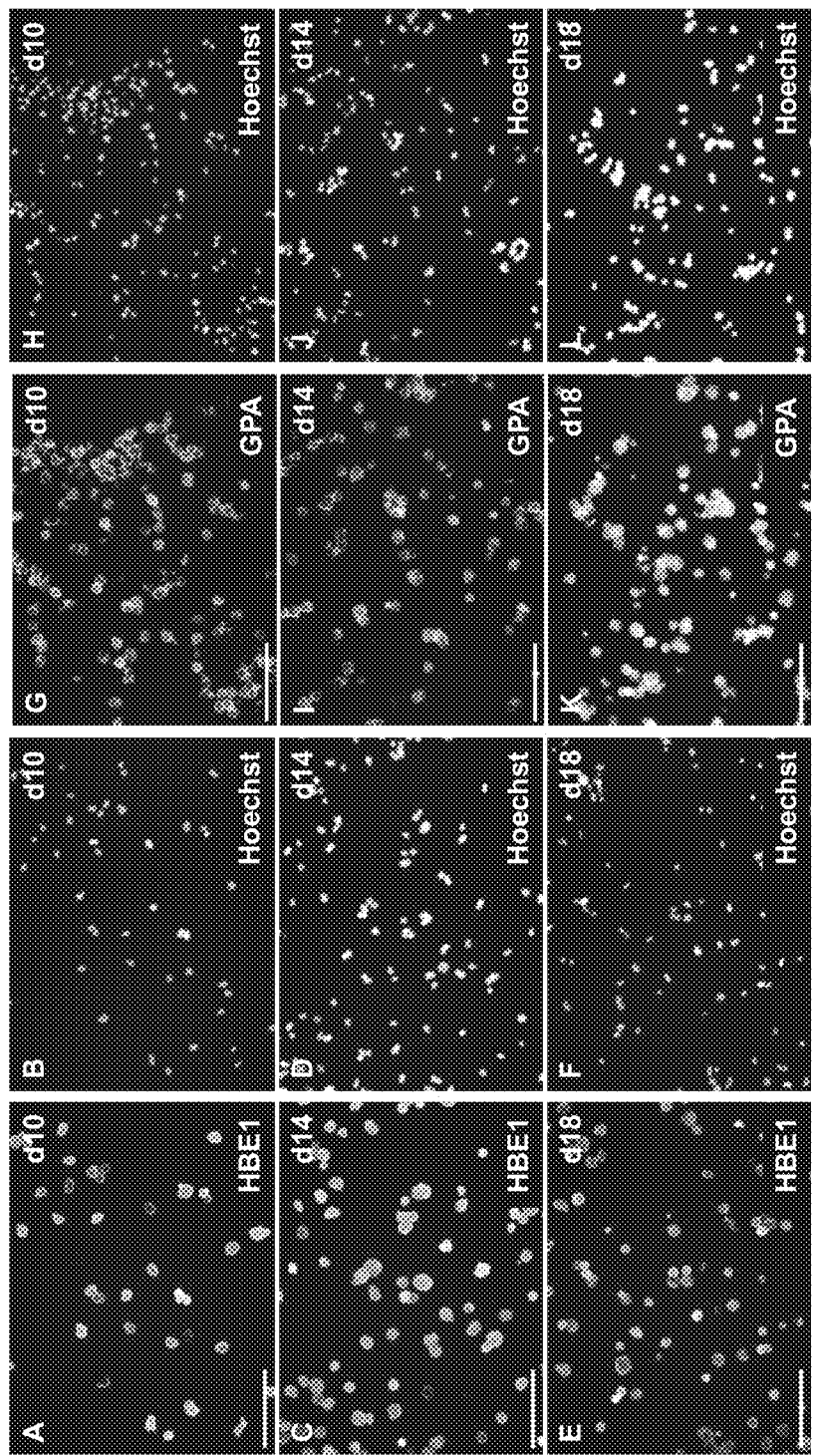
FIG. 20 is fluorescent micrographs obtained by fluorescent immunostaining of an embryonic erythroblast-containing cell population derived from human ES cells (KhES-1 strain) at Day 10, Day 14, or Day 18 after the start of suspension culture (step (1)) in Example 6. A and B, C and D, or E and F represent an ε-globin (HBE1) staining image and its nuclear staining image at Day 10, Day 14, or Day 18, respectively, after the start of suspension culture (step (1)). G and H, I and J, or K and L represent a glycophorin A (GPA) staining image and its nuclear staining image at Day 10, Day 14, or Day 18, respectively, after the start of suspension culture (step (1)). The scale bars in A, C, E, G, I, and K each indicate 100 μm.

FIG. 20 shows the results of staining images. About 80% or more of the cells obtained at Day 10 after the start of suspension culture (step (1)) were found ε-globin positive and glycophorin A positive (FIGS. 20A, B, G, and H). The cell population abundantly containing embryonic erythroblasts was demonstrated to be successfully produced from human ES cells by the production method of the invention. In addition, about 80% or more of the cell population obtained at Day 14 or 18 after the start of suspension culture (step (1)) was also found ε-globin positive and glycophorin A positive (FIGS. 20C, D, I, and J and FIGS. 20E, F, K, and L). It has been demonstrated that the percentage of embryonic erythroblasts in a cell population after the cell population is continuously cultured can be kept high by the production method of the invention.

<To Evaluate Cell Population by Real-Time PCR>

The percentage of expression of the β-globin gene family expressed in cells of the above cell population at Day 10, 14, or 18 after the start of suspension culture (step (1)) was checked by real-time PCR. The real-time PCR was performed by the same protocol as in Example 1. The TaqMan probes used were human probes designated in Table 2.

The gene product containing a TaqMan probe target sequence for each member of the β-globin gene family, namely ε-globin, γ-globin, or β-globin, was used to draw a standard curve. Then, the mRNA copy number for each β-globin gene family member expressed was quantified. The value obtained by dividing the copy number for each β-globin gene family member by the total β-globin gene family copy number was shown as the percentage of expression of each β-globin gene family member.

Table 8 shows the results. In any of the cell population at Day 10, 14, or 18 after the start of suspension culture (step (1)), about 60% or more of all the β-globin gene family were ε-globin gene, an embryonic erythroblast marker. According to the production method of the invention, the cell population with increased levels of expression of ε-globin was demonstrated to be successfully produced from human ES cells. In addition, according to the production method of the invention, it has also been demonstrated that the expression of ε-globin can be kept high even after the cell population is continuously cultured. The total of three different human pluripotent stem cell lines including one human ES cell strain and two human iPS cell strains were used to successfully produce a cell proportion containing embryonic erythroblasts at a high percentage. Therefore, the production method of the invention can be said to be a highly-reproducible method.

TABLE 8

Relative expression levels (%) of the β-globin gene family in human ES cells (KhES-1 strain)

|  | Day 10 | Day 14 | Day 18 |
|---|---|---|---|
| ε-Globin (HBE1) | 74 | 66 | 70 |
| γ-Globin (HBG2/1) | 26 | 34 | 30 |
| β-Globin (HBB) | 0 | 0 | 0 |

The invention claimed is:

1. A method for producing a cell population containing embryonic erythroblasts, comprising:
    (1) subjecting pluripotent stem cells to suspension culture to form a cell aggregate;
    (2) obtaining the cell population from the cell aggregate obtained in step (1),
    wherein step (2) comprises step (2a) of subjecting the cell aggregate to adhesion culture, and
wherein:
    (i) a total period of the suspension culture in step (1) is 8 h or more and about 6 days or less,
    (ii) step (2a) is performed in the presence of at least one selected from the group consisting of erythropoietin, erythropoietin receptor-activating substances, and erythropoietin receptor-mediated signaling pathway-activating substances, and
    (iii) step (2a) is performed in the presence of a ROCK inhibitor.

2. The production method according to claim 1, wherein step (2) further comprises step (2b) of collecting the cell population.

3. The production method according to claim 1, wherein at least 70% of cells included in the cell population are the embryonic erythroblasts.

4. The production method according to claim 1, wherein at least 50% of B-globin gene family expressed in cells of the cell population is E-globin gene.

5. The production method according to claim 1, wherein step (1) is carried out using non-cell-adherent cultureware.

6. The production method according to claim 1, wherein step (2a) is carried out using cell-adherent cultureware or in the presence of feeder cells.

7. The production method according to claim 6, wherein the feeder cells are bone marrow stromal cells or a bone marrow stromal cell-derived cell line.

8. The production method according to claim 1, wherein step (1) follows a step of dispersing the pluripotent stem cells.

9. The production method according to claim 1, wherein step (1) comprises a step of centrifuging the pluripotent stem cells.

10. The production method according to claim 1, wherein step (2a) is performed in the presence of at least one selected from the group consisting of stem cell factor, interleukin 3, interleukin 11, hydrocortisone, and insulin-like growth factor.

11. A cell population obtained by the production method according claim 1.

12. A cell culture composition comprising: the cell population according to claim 11; and a medium.

13. The cell culture composition according to claim 12, wherein the medium is free of at least one selected from the group consisting of interleukin 3, interleukin 11, hydrocortisone, and insulin-like growth factor.

* * * * *